(12) United States Patent
Murray et al.

(10) Patent No.: US 10,436,907 B1
(45) Date of Patent: Oct. 8, 2019

(54) ACTIVE CHRISTIANSEN EFFECT LIDAR SYSTEM AND METHOD

(71) Applicant: Arete Associates, Northridge, CA (US)

(72) Inventors: James Murray, Longmont, CO (US); Paul Lundquist, Longmont, CO (US); Jason Seely, Longmont, CO (US); Steve Rako, Longmont, CO (US); Micah Boyd, Longmont, CO (US)

(73) Assignee: Arete Associates, Northridge, CA (US)

( * ) Notice: Subject to any disclaimer, the term of this patent is extended or adjusted under 35 U.S.C. 154(b) by 636 days.

(21) Appl. No.: 14/881,141

(22) Filed: Oct. 12, 2015

Related U.S. Application Data

(60) Provisional application No. 62/062,879, filed on Oct. 11, 2014.

(51) Int. Cl.
| | |
|---|---|
| G01S 17/89 | (2006.01) |
| G01N 15/06 | (2006.01) |
| G01N 21/53 | (2006.01) |
| H04N 5/33 | (2006.01) |
| G06T 7/00 | (2017.01) |
| G06T 7/60 | (2017.01) |
| G06T 15/04 | (2011.01) |
| G06T 15/08 | (2011.01) |
| H04N 5/28 | (2006.01) |

(52) U.S. Cl.
CPC .............. *G01S 17/89* (2013.01); *G01N 15/06* (2013.01); *G01N 21/53* (2013.01); *G06T 7/0048* (2013.01); *G06T 7/0057* (2013.01); *G06T 7/602* (2013.01); *G06T 15/04* (2013.01); *G06T 15/08* (2013.01); *H04N 5/28* (2013.01); *H04N 5/33* (2013.01); *G01N 2015/0693* (2013.01); *G01N 2201/06113* (2013.01); *G06T 2207/10032* (2013.01); *G06T 2207/10048* (2013.01); *G06T 2207/30181* (2013.01); *G06T 2215/12* (2013.01)

(58) Field of Classification Search
CPC ............................... G01S 17/89; G01N 15/06
See application file for complete search history.

(56) References Cited

U.S. PATENT DOCUMENTS

| | | | |
|---|---|---|---|
| 6,690,474 B1 * | 2/2004 | Shirley | G01B 11/2527 356/512 |
| 2010/0021177 A1 * | 1/2010 | Osterberg | A61B 5/0059 398/141 |
| 2012/0274937 A1 * | 11/2012 | Hays | G01S 17/58 356/337 |
| 2013/0109963 A1 * | 5/2013 | Zhu | A61B 8/0825 600/427 |

(Continued)

*Primary Examiner* — Jeffery A Williams
(74) *Attorney, Agent, or Firm* — Furman IP Law

(57) ABSTRACT

Provided herein are systems and methods for an active sensing instrument actively utilizing the Christiansen effect to sense and adapt to suspended scatterers such as dust. The instrument enhances detection of remote surfaces that are partially or fully obscured at visual wavelengths due to those suspended scatterers. The system also may be used to measure properties and spatial distributions of the suspended scatterers themselves. Though the system is broadly applicable to remote detection through scattering media, it is particularly drawn to remote sensing through dust particles in the atmosphere as may be produced from helicopter fly-overs, dust storms, or other events that draw up substantial concentrations of mineral-based dust particles into the air.

9 Claims, 18 Drawing Sheets

(56) References Cited

U.S. PATENT DOCUMENTS

2015/0185077 A1* 7/2015 Malcolm ............... G02F 1/3532
356/402
2015/0293330 A1* 10/2015 Gutierrez ........... G02B 13/0015
359/811

* cited by examiner

ACTIVE CHRISTIANSEN EFFECT LIDAR SYSTEM AND METHOD

RELATED APPLICATIONS

The application claims priority to U.S. Provisional Patent Application Ser. No. 62/062,879, entitled "CHRISTIANSEN LIDAR," and filed Oct. 11, 2014, the disclosure of which is hereby incorporated by reference in its entirety for all purposes.

FIELD OF THE TECHNOLOGY

The present disclosure relates to LIDAR and laser detection systems operating in volumes with spatial distributions of suspended scatterers.

SUMMARY OF THE DESCRIPTION

Provided herein are systems and methods for an active sensing instrument actively utilizing the Christiansen effect to sense and adapt to suspended scatterers such as dust. The instrument enhances detection of remote surfaces that are partially or fully obscured at visual wavelengths due to those suspended scatterers. The system also may be used to measure properties and spatial distributions of the suspended scatterers themselves. Though the system is broadly applicable to remote detection through scattering media, it is particularly drawn to remote sensing through dust particles in the atmosphere as may be produced from helicopter fly-overs, dust storms, or other events that draw up substantial concentrations of mineral-based dust particles into the air.

In one aspect, the disclosure describes an optical system, including one or more tunable lasers operable to provide radiation beams having selectable wavelengths within a wavelength range. The optical system further includes a beam scanning mechanism operable to direct one or more radiation beams through sequences of angles, where the beam scanning mechanism includes an exit aperture for emission of the radiation beams. The optical system further includes an imaging system, sensitive to the wavelength range, that generates digitized images of scattering from particles or surfaces impinged by the radiation beams, where the imaging system further includes an entrance aperture different from the exit aperture. The optical system further includes a wavelength controller configured to select wavelengths of the one or more tunable lasers to optimize the digitized images of scattering from particles or surfaces impinged by the radiation beams. The optical system further includes an image processor that uses the digitized images to generate calculated volumetric coordinates of points where the radiation beams impinge surfaces.

Other embodiments and features of the present disclosure will be apparent from the accompanying drawings and from the detailed description which follows.

BRIEF DESCRIPTION OF THE DRAWINGS

The embodiments are illustrated by way of example and not limitation in the Figures of the accompanying drawings in which like references indicate similar elements.

DESCRIPTION

Figure 1:
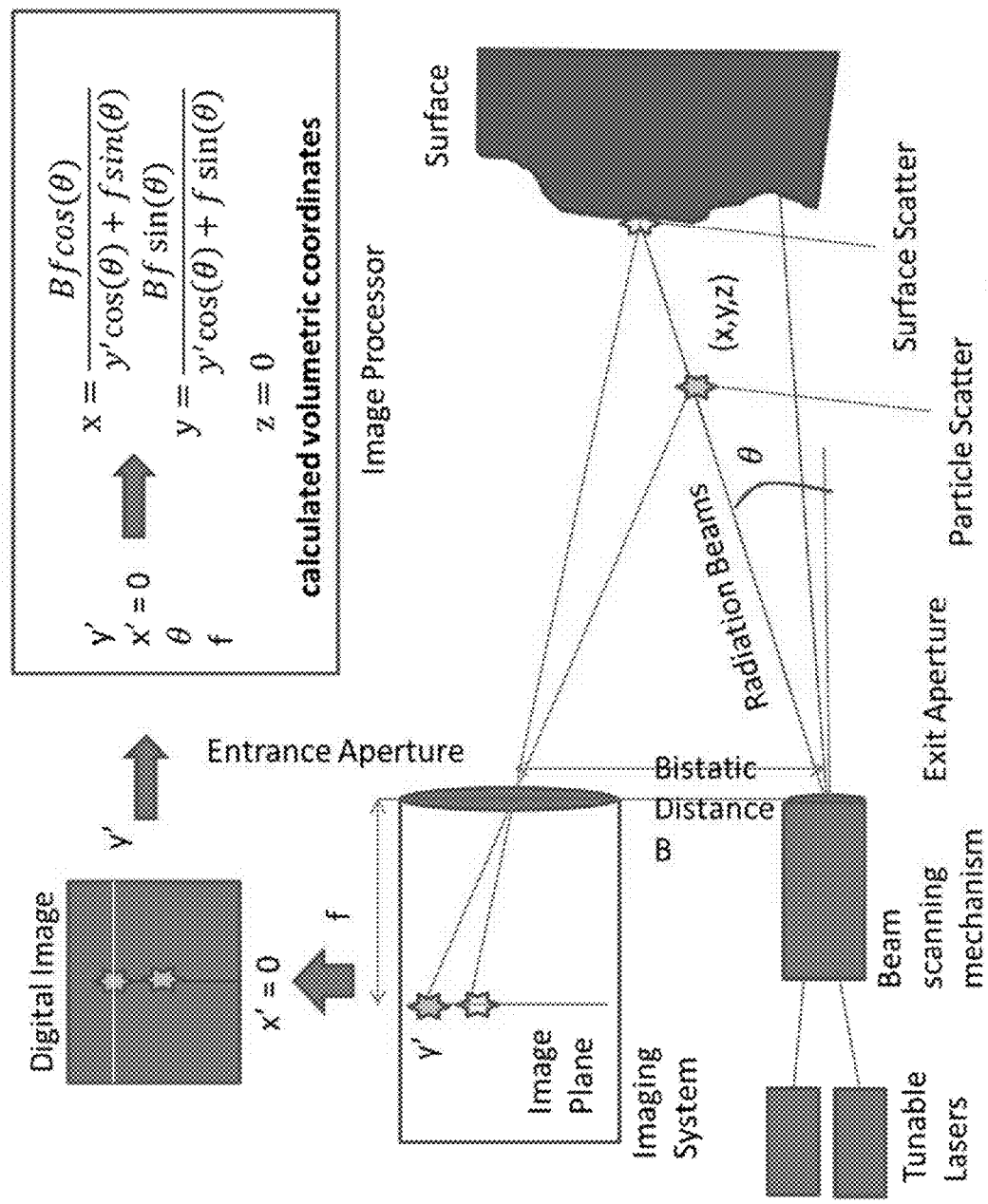
FIG. 1 shows a system for using a digital image for calculating volumetric coordinates of points via where radiation impinges on surfaces.

The following patent description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

An active Christiansen effect Long-Wave IR (LWIR) LIDAR detection system has significant benefits for pilotage in Degraded Visual Environments (DVE). These include, but are not limited to real-time 3D detection and mapping of terrain and hazards in the vicinity of the aircraft. Another example is direct measurement of the dust cloud (or other DVE and environmental features) that enable "model-based" high-level fusion of passive and active sensors to remove or erase DVE obscurants from the visualization solution. By choosing a transmitter wavelength in the LWIR, and more specifically at wavelengths where the Christiansen effect minimizes scatter, the penetration depth through DVE can be dramatically improved.

The Christiansen effect is the spectrally dependent enhanced transmission that occurs in a media consisting of particles within a matrix medium when the index of refractions of the particles and the matrix are equal. When the indices of refraction are matched, the scattering contribution to attenuation is suppressed. In air this can occur at wavelengths near absorption lines of dust or aerosols when the index of refraction crosses unity. For silicates this occurs at around 7.4 um. When the index of refraction is nearly equivalent in both air and in the particle, attenuation is still dominated by absorption, but scattering from silicate dust particles is reduced. The wavelength where attenuation is minimized depends on both mineral constituents and the concentrations. For many minerals, the wavelength where attenuation is minimized may be between 8.0 μm and 8.5 μm. Any reference herein to a particular wavelength and/or a particular composition of particles for attenuation minimization may be changed for particular embodiments, including tunable wavelength bands for expected composition of particles.

In many situations a suspension of scatterers may include multiple material types so that no one selected wavelength may be chosen to precisely eliminate scattering. However an optimal wavelength can often be selected to minimize scattering or otherwise optimize the sensors performance.

FIG. 1 shows a system for using a digital image for calculating volumetric coordinates of points via where radiation impinges on surfaces. The system shows a typical geometry for calculating these points. The particle scatter at (x, y, z) produces different scatter beams through the entrance aperture, creating different coordinates x' and y' on the digital image. Based on the known angle of illumination by the selected radiation beam, the volumetric coordinates can be calculated.

In the described system one or more tunable lasers, having selectable wavelengths, are used to illuminate paths through a volume with radiation beams that are tuned to specific wavelength within a wavelength range. The beam paths are sequentially selected by a beam scanning mechanism. The scanning mechanism is described further herein and produces beams within the calculated volume of space.

A separate imaging system that has sensitivity over the wavelength range is used to image the beam paths in a bistatic configuration. In such a configuration, the imaging system's entrance aperture is displaced from the output aperture or exit aperture or apertures corresponding to the radiation beams. Based on the relative orientation and position of the imaging system and the known paths for each of the radiation beams, any scattered light that is imaged by the imaging system may be associated with a 3D location. Scattered light may be scattered from particles or surfaces.

The imaging system produces a digital image. For each radiation beam line in the digital image, the angle that was selected (θ) by the beam scanning mechanism is known. Based on the angle selected for the radiation beam, optical parameters, the bistatic distance B, and coordinates within the digital image (x', y'), the volumetric parameters (x, y, z) may be calculated.

Figure 2:
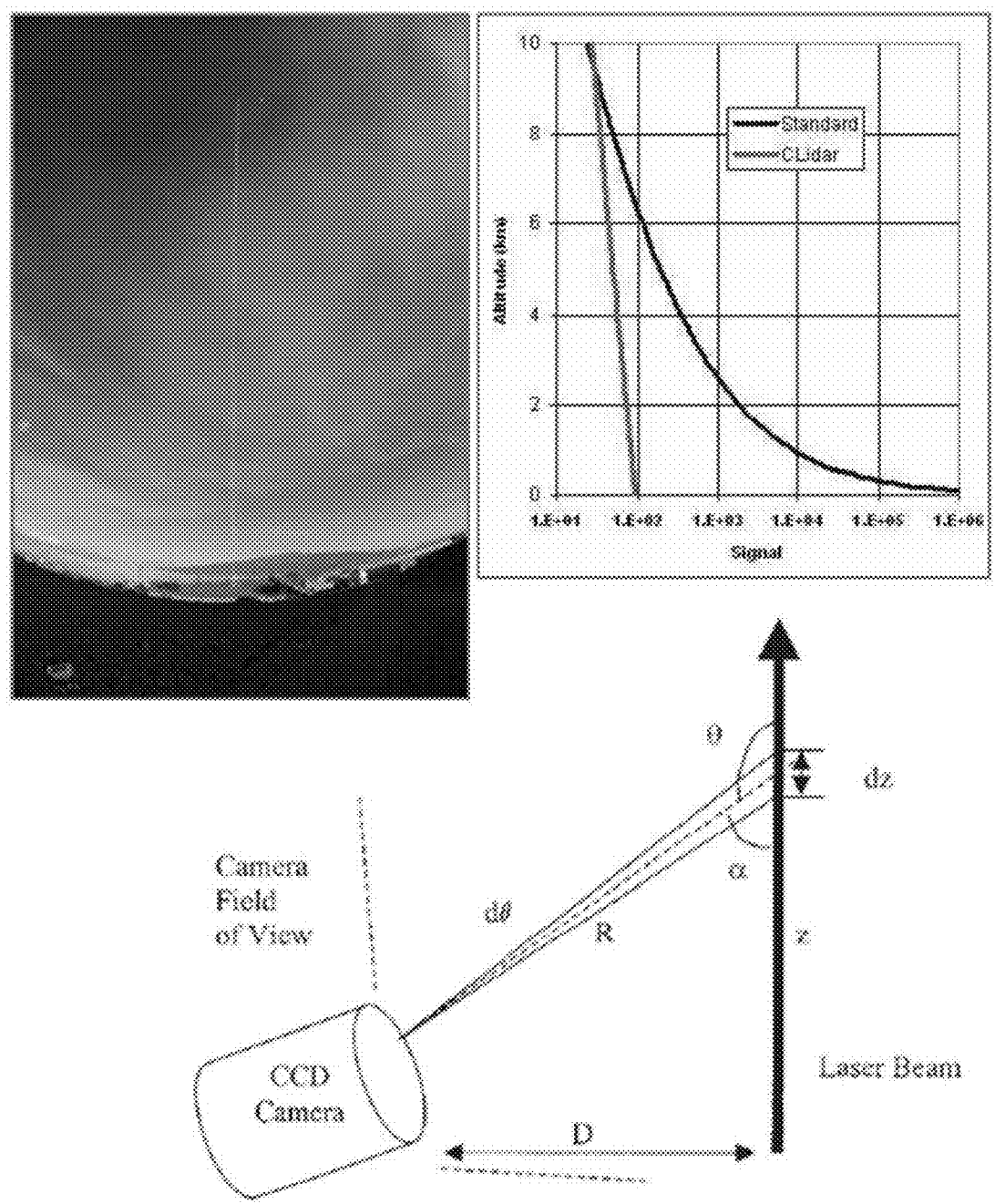
FIG. 2 illustrates an example where backscatter from a stationary green laser is used to measure scattering concentrations as a function of altitude in atmospheric LIDAR.

FIG. 2 illustrates examples of prior uses of LIDAR.

Conventional atmospheric measurement LIDAR uses backscatter from a stationary green laser to measure scattering concentrations as a function of altitude in atmospheric LIDAR.

Alternatively, systems using an image of a scatter from a laser beam for LIDAR information have been developed and are known as CCD LIDAR. Here the CCD imager is arranged in a bistatic configuration with the transmitter and is arranged to view the laser beam from an angle so that the altitude associated with laser scatter may be calculated based on the geometric configuration of the camera. Unlike time-domain LIDARS, using geometric configurations to calculate altitude information doesn't require high bandwidth detection or high-bandwidth modulation or encoding on the laser beam. The laser need not be pulsed and, for LWIR wavelengths, this enables the use relatively mature laser technology.

Additionally, since, via using an imaging sensor, the altitude or range along the laser beam path is mapped to separate pixels, there is an opportunity to better manage dynamic range constraints. In typical time domain (or Fourier domain) LIDAR systems, where a single detector is used to collect backscatter from all ranges, challenges occur in measuring high intensity returns from near range scatterers and also measuring them much weaker returns from long range scatterers during the same data collection event. The large dynamic range is due to the $1/z^2$ radiometric fall-off in scattered light collected by a fixed aperture (z is distance from aperture) and due to the Beer's law exponential attenuation of light through a distribution of scatterers. When a single detector is used, gains may be difficulty to adjust for both high-intensity and weak return beams. The gains adjusted for detection of distant weak returns may result in saturation from strong near-range returns. On the other hand, reducing gain may allow measurement of strong near-range returns but drive weak returns below the system's minimum detectable signal strength.

By using an imaging array to measure backscatter from a radiation beam, the detection system's optical transmission may be designed to have a varying dependence on range. Additionally, the spatial resolution is also generally dependent on range. At long ranges, spatial resolution is reduced to maintain high detectability. This can be understood by realizing that at longer ranges, increased distance along the radiation beam line is mapped to a single camera image pixel. In other words, images at a greater distance look smaller, and for long ranges may be mapped to a single image pixel on the imaging sensor. Additionally, the imaging system may be configured so that very-near-range scatter is outside the imaging system's field of view and doesn't affect any of the detectors. For example, given knowledge of the transmitted beam's path, the imaging system may map the return beam from near-range scatterers away from an area of the image sensor with sensitive pixels.

CCD LIDAR's benefits may be used with the present disclosure's innovations including the active wavelength scanning and modification while probing through a volume of unknown scatterers.

Figure 3:
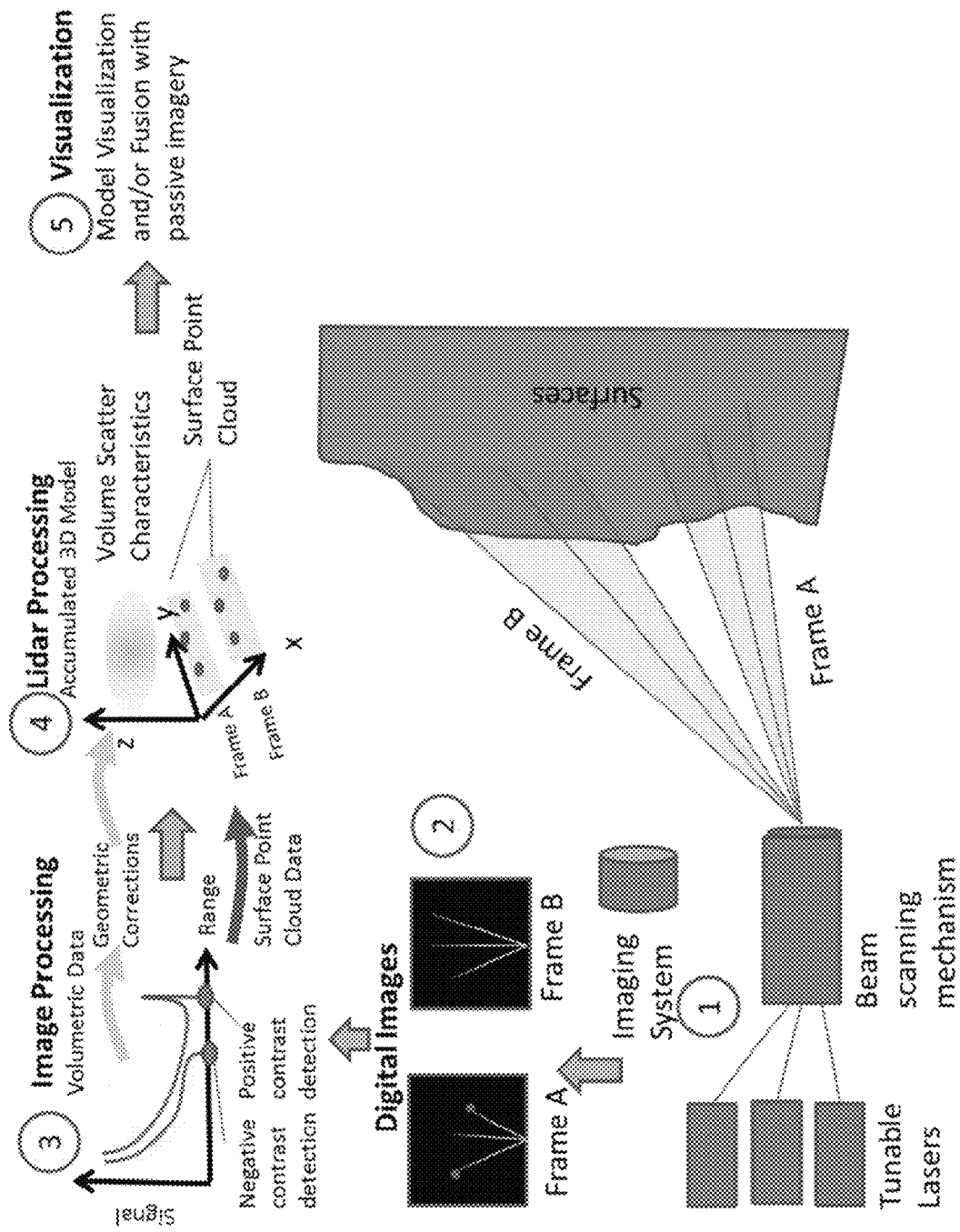
FIG. 3 illustrates functional aspects of an exemplary embodiment of an Active Christiansen Effect LIDAR Detection System.

FIG. 3 illustrates functional aspects of an exemplary embodiment of an Active Christiansen Effect LIDAR Detection System. One or more tunable lasers are selected to provide laser light at a particular wavelength via selection criteria and processes as described further herein. The created laser light is fed into the beam scanning mechanism to provide one or more radiation beam lines at any one instant in time, at portion 1 of the system. Radiation lines denoting "Frame A" capture an instant in time, followed by "Frame B". These radiation beams impinge on various surfaces and are returned by those surfaces. The returned light is captured by the receiving aperture offset by the bistatic distance of the system. The returned light is directed by the imaging system to the imaging sensor, except as further described herein such as filtering or steering to reduce dynamic range issues for near/far scatterers.

The imaging system captures digital images through a return aperture into multiple frames corresponding to different instants in time, as illustrated at portion 2 of the system. The image processor calculates the intensity of the received scattered light as a function of range along each beam line as depicted at portion 3 of the system. This data is used to extract a point cloud associated with radiation beam intercepts with surfaces.

The detection of these surface points may be somewhat complex due to the variability in volumetric scatter, beam attenuation and surface scatter. For example, surface scatter may result in a bright backscatter and positive contrast detection may be used to identify the surface point. However, if the surface backscatter doesn't direct sufficient light back towards the detector, and if there is sufficient volumetric scatter, a negative contrast detection may be used to identify a surface point. In addition to extracting a surface point cloud, data associated with volumetric scattering may be collected.

In one embodiment, for each frame and each radiation beam line, this data associated with volumetric scattering is collected for ranges less than the range to any surface points. After corrections for geometric factors and estimates for outgoing and incoming attenuation, this volumetric scattering data may be used to extract relative scatterer density distributions from the scans.

In several embodiments, the process of extracting a relative scatterer density distribution requires data that is accumulated from one or more previous frames and stored within a volumetric model. For example, several frames may be used to illuminate with different directions or wavelengths, as described further herein. The surface point cloud data and extracted scatterer characteristics may be accumulated in a volumetric model, at portion 4 of the system. Ultimately this model may be used for visualization and this visualization may include fused passive imagery, at portion 5 of the system.

In order to more rapidly interrogate a volume, multiple radiation beams may be simultaneously used, provided that they are arranged to illuminate different regions of the image plane in the imaging system. Generally, each radiation beam line should illuminate a distinct path in the image so that the image processor may process each beam line independently. FIG. 3 shows exemplary beam paths on the image for Frame A and Frame B.

In embodiments where a very high number of radiation beam lines are imaged in a single frame, multiple detector arrays may be used within the imaging system. In one embodiment, each detector array may have separate spectral filters or polarization filters. In one embodiment, the wavelength controller may select slightly different wavelengths and or polarizations for subsets of the radiation beams. In this embodiment, digital images that are spectrally sensitized to different subsets of the radiation beams may be produced so that a greater number of radiation beams may be processed in each frame without significant interference from overlapping radiation beam images on the image sensor.

The profile of a beam path detected by the camera (or imaging system) may be considered effectively a record of the scattered light that is shed by the beam as it propagates through an obscurant laced atmosphere. This record of the obscurant atmosphere is thus recorded until the beam is intercepted by a hard target or exits the camera FOV. As described further herein, in contrast, time-domain LIDAR detects a "LIDAR waveform" over time including information about the light scattering history as a function of time, such as on a single pixel. Alternatively, by using a CCD camera or other imaging sensor, a sensor detects the LIDAR waveform by imaging the beam path over the exposure time of the camera. This enables a CW laser source to be used as the transmitter while obtaining the same "range" information as a time-of-flight LIDAR system would with a pulsed laser and a high-speed digitized detector. The CW laser may include a relatively low rate intensity strobe modulation to allow multiple exposures within the cameras integration time that may correspond to separate angular configurations set by the beam scanning mechanism. This allows each laser to produce multiple radiation beams for each digital image.

It should be noted that though many different types of tunable laser may be considered depending on the specific application and the waveband associated with the reduced attenuation, for the case where it is desired to perform remote sensing through mineral dust particles, quantum cascade lasers (QCLs) appear to provide particular benefits in their relatively compact size and higher power. When multiple radiation beams are needed an array of micro-chip QCLs may be delivered to the beam scanning mechanism.

Figure 4:
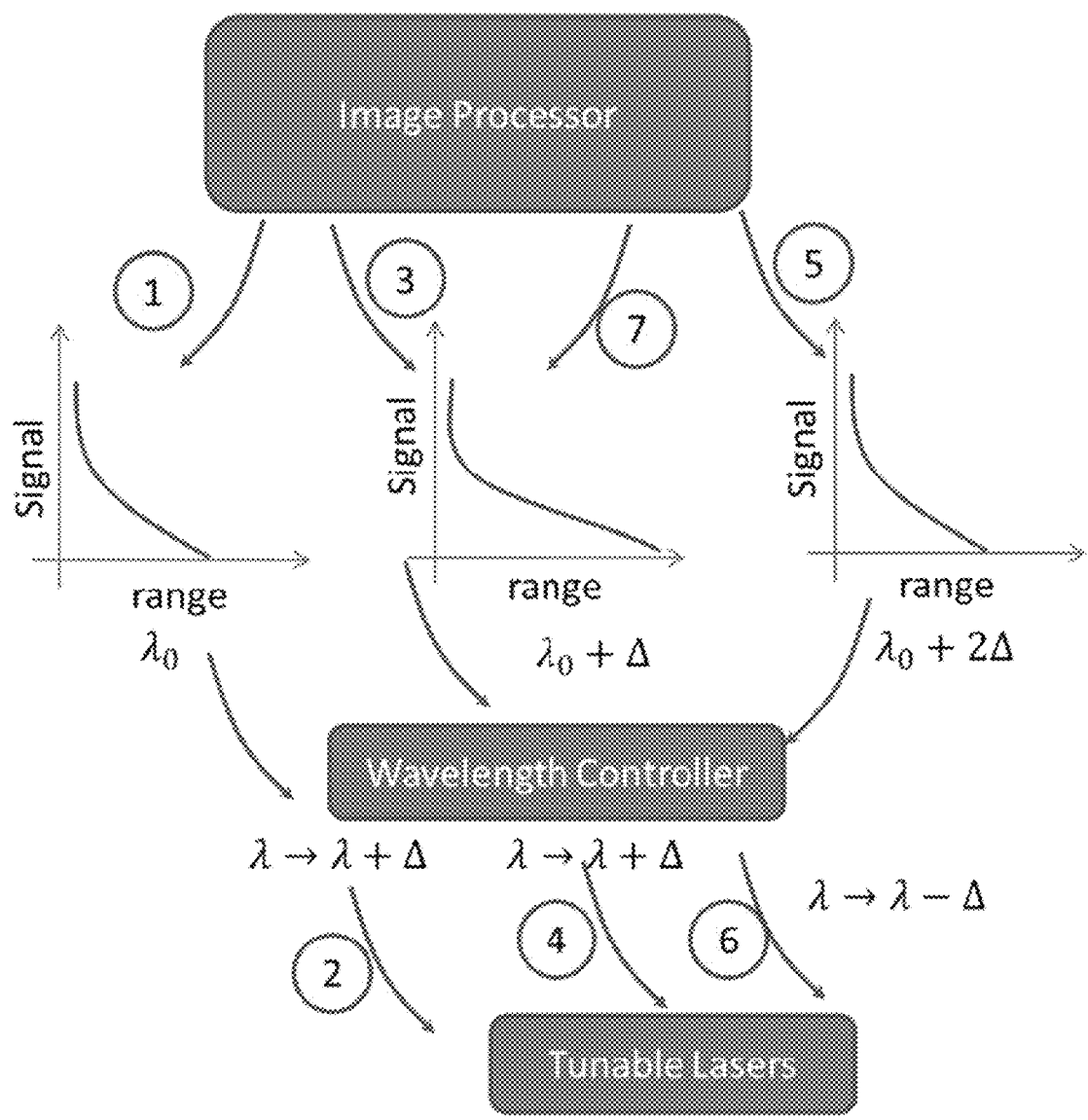
FIG. 4 illustrates an exemplary process by which a wavelength controller may be used to optimize the digital images that are processed by the image processor.

FIG. 4 illustrates an exemplary process by which a wavelength controller may be used to optimize the digital images that are processed by the image processor.

A functional relationship between signal strength and calculated range may be created from the image processor after a digital image is received. When the image processor processes a digital image provided by the imaging system, a scattering signal may be extracted for each imaged radiation beam as a function of range. A curve representing a scatter signal as a function of range may be calculated and plotted such as those shown in FIG. 4. This curve may be a composite curve based on multiple beam lines. In the curve, the range dimension may represent the distance from the exit aperture, the entrance aperture or some other representative distance.

In one embodiment, the process of forming a composite curve for analysis herein may include a statistical combination of measured beam lines. In one embodiment, some measured beam lines may be excluded from statistical combination. For example, measured beam lines may be excluded based on intercepts with surfaces at near ranges.

The image processor processes one or more digital images to generate a range dependent scattering signal (item 1). The wavelength controller may select to increase the wavelength by an amount $\Delta$ (item 2), which results in the tunable lasers increasing their output wavelength. After the image processor processes digital images that have been collected by the imaging system with the increased wavelength, a new range dependent signal curve is generated (item 3) which may have larger signals at long ranges. The wavelength controller may select an even longer wavelength (item 4), which results in the image processor producing updating the range dependent signal curve. In this example, the resulting range dependent signal curve after item 5 shows a decreased signal strength at longer ranges. Consequently, the wavelength controller selects to reduce the wavelength range in item 6, for example back to the initially increased value for the wavelength. In item 7, with the wavelength reduced, the subsequent signal versus range graph shows increased signal again at longer ranges. This sequence of illustrated items is an exemplary embodiment of converging to an optimal wavelength in subsequent digital images.

Though the intent may be often to increase the sensing range, there are several ways in which the illustrated range-dependent signal curves may be used to optimize the digital images. A signal threshold may be set, and the maximum range where the curve crosses that threshold may be used as an optimization parameter. A history of collected or processed data may also be used to determine whether the laser wavelengths need adjustment and how much adjustment to make. For example, range dependent signal curves from multiple measurements may be accumulated so that an average curve is used and the wavelength step size may be selected based on the standard deviations of the collection of curves. Temporal filtering and rate limits may also be used to manage the rate of adjustment. Modifications of the algorithm are also possible for the case where low scattering levels exist and the brightest points in the scene correspond to laser illumination of solid surfaces.

In embodiments described herein, the wavelength controller iteratively selects wavelengths of the tunable lasers to maximize intensity of images of scattering from particles or surfaces impinged by the radiation beams, where the particles or surfaces are selected to have calculated volumetric coordinates outside of a pre-selected volume. Because decreased attenuation from scatter may be desired, near range scatter may not be included in the optimization process. These excluded near ranges may be defined include the entrance and exit aperture and all points within some selected threshold range from either the exit aperture or entrance aperture.

Via more sophisticated algorithms, a maintained model of volumetric and scattering and absorption information may also be used to select wavelengths of one or more tunable lasers to maximize a calculated intensity at a range threshold. In this approach, the accumulated 3D model shown in FIG. 3 iteratively refines a 3D wavelength dependent map of scatterers and uses this data to compute an optimal wavelength to transmit the most light at a specific location. Algorithms for searching a volume of scatterers and searching wavelengths for use depending on those scatterers are described further herein.

Figure 5:
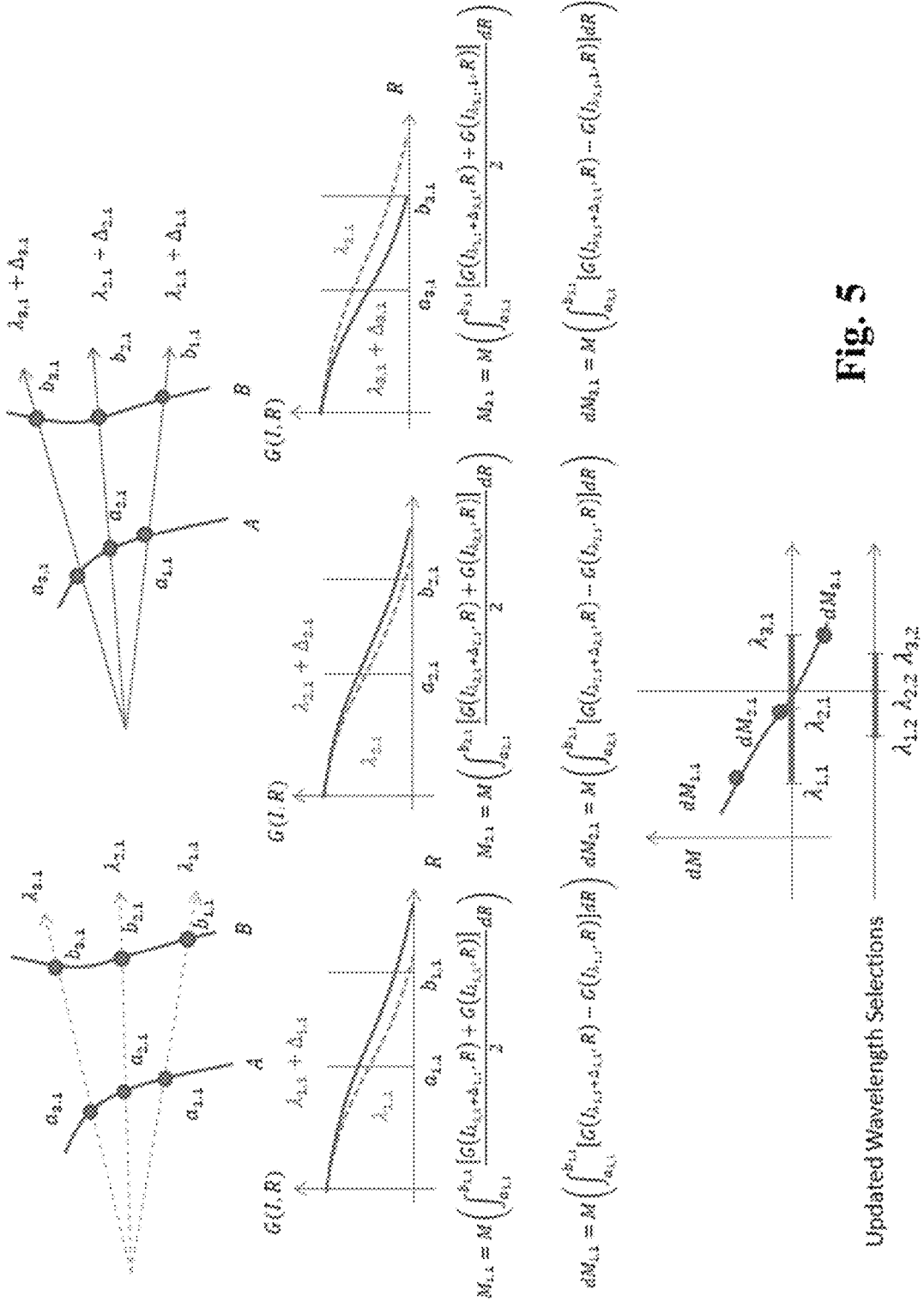
FIG. 5 illustrates an exemplary embodiment of a sequence of decisions for selecting wavelengths for each of the tunable lasers of the system.

FIG. 5 illustrates an exemplary embodiment of a sequence of decisions for selecting wavelengths for each of the tunable lasers of the system. From the top of the Figure, briefly described, beams denoted by their wavelengths ($\lambda_{1,1}$, $\lambda_{2,1}$, $\lambda_{3,1}$) are shown impinging on or through the surface or range "A" at points $a_{1,1}$, $a_{2,1}$, $a_{3,1}$ an surface or range "B" at points $b_{1,1}$, $b_{2,1}$, $b_{3,1}$. These various beam directions and wavelengths are noted by the subscripts on the wavelength of the beam, as described further herein.

After the light is received back through the entrance aperture, the collected light for each radiation beam line is calculated as a function of range along the radiation beam line to create signal versus range relationships for the various returned beams. Exemplary graphs are shown as graphs of G(I,R).

The information from these signal-range relationships is used to calculate metrics and gradient metrics comparing the received light before and after a wavelength shift such as $\lambda_{1,1}+\Delta_{1,1}, \lambda_{2,1}+\Delta_{2,1}$, and $\lambda_{3,1}+\Delta_{3,1}$. Wavelength shifts are determined based on decisions and searching methods described further herein. The gradient metrics, $dM_{i,j}$, integrate differences in light over range segments before and after wavelength shifts. These gradient shift calculations are thereafter used to determine the next updated wavelength selections to be made, as shown in the bottom of the Figure and also described further herein.

As an exemplary embodiment, three different radiation beams are shown at the top of FIG. 5, each having separate wavelengths $\lambda_{1,1}$, $\lambda_{2,1}$, and $\lambda_{3,1}$. An analysis segment for each beam is defined by the ranges at which the beam intercepts these two surfaces (e.g., $a_{1,1}$, $a_{2,1}$, $a_{3,1}$ and $b_{1,1}$, $b_{2,1}$, $b_{3,1}$). For an exemplary sequence of radiation beams, a pre-selected keep-out volume consists of a near keep-out volume consisting of all points closer to the exit aperture than surface A, for example for reducing near-range scatter signals, as described further herein. The pre-selected far keep-out volume consisting of all points further than surface B.

The far keep-out surface may be defined to specifically eliminate surface scatter from the analysis, in which case it may be updated over time. The near-range keep-out surface may be updated over time as well so that wavelength refinement may be performed for longer range LIDAR penetration. Alternatively, if the analysis will be based on physical surface scatter, then surface A may be calculated for a position that is only slightly nearer than the measured physical surface allowing for a focused range of the keep-out volume being searched and allowing more dynamic range of the imaging sensor to be used via correct image sensor gain adjustment, as described further herein.

The tunable lasers are selected to span a range of specific wavelengths representing a search band. In one embodiment, a search band may be searched via a wavelength measurement pair (or group) that consists of two or more measurements by each tunable laser. As described further herein, a wavelength pair is used for ease of discussion. In the first measurement, the tunable lasers are configured for a first selection of wavelengths ($\lambda_{1,1}, \lambda_{2,1}, \lambda_{3,1}$). For a subsequent measurements, each of the tunable lasers are slightly shifted to wavelengths $\lambda_{1,1}+\Delta_{1,1}, \lambda_{2,1}+\Delta_{2,1}$, and $\lambda_{3,1}+\Delta_{3,1}$, where the $\Delta_{j,k}$ values are generally smaller than the separation between the wavelengths of each tunable laser, e.g., to avoid overlapping wavelengths.

During the wavelength selection process, the wavelength shifts and scanning are advantageously performed quickly enough that the volumetric characteristics sampled by each radiation beam do not significantly differ between sample times.

A geometric function of that curve G(I(R),R)=G(R) may be calculated to facilitate analysis. This geometric function may include compensation for optical system vignetting, a range dependent collection efficiency and baseline estimates for attenuation. A simple geometric function may be G(I(R), R)=$R^2$I(R) which compensates for the expected 1/$R^2$ aperture collection efficiency drop off with range.

After a wavelength pair measurement is completed, integrals of the geometric function along the analysis segments for each radiation are calculated. This is calculated using geometric functions before and after the wavelength shift (e.g., $\lambda_{1,1}+\Delta_{1,1}, \lambda_{2,1}+\Delta_{2,1}$, and $\lambda_{3,1}+\Delta_{3,1}$). For each radiation beam denoted by wavelength $\lambda_{j,k}$ representing beam number "j" and search iteration "k", the average of the integrated geometric function before and after the positive wavelength shift of $\lambda_{1,1}+\Delta_{1,1}, \lambda_{2,1}+\Delta_{2,1}$, and $\lambda_{3,1}+\Delta_{3,1}$ are stored in the metric parameters $M_{j,k}$ which provide a metric for how much light was scattered from the analysis segments at different wavelengths before and after the wavelength shift.

The integrated difference in geometric functions introduced by the wavelength shifts are stored in the gradient metric parameters $dM_{j,k}$. Metric parameters and gradient metric parameters are used to refine the wavelength search band and the pre-selected keep out volume via selection processes described further herein.

For example, at the bottom of FIG. 5, gradient metric parameters are plotted as a function of wavelength for an initial wavelength search band covered by the selected wavelengths of the tunable lasers. In this example, an increase in wavelengths at $\lambda_{1,1}$ results in an increase in the scattered light with the analysis segment along the radiation beam with beam number j=1. An increase in wavelengths at $\lambda_{3,1}$ results in a decrease in the scattered light with the analysis segment along the radiation beam with beam number j=3.

Thereafter, the wavelength search band can be modified and/or reduced for further searches. Through interpolation of gradient metric parameter curve, a zero crossing can be estimated where wavelength variations should have little impact on scattering from a similar analysis segment and the total scattered light should be maximized. In one embodiment, a subsequent wavelength search band is selected to be approximately centered around the zero-crossing. As a matter of design choice, the subsequent wavelength search band may also be contracted to span a narrower range of wavelengths as well. For example, wavelengths may be selected that surround a zero-crossing for the gradient metric. Zero-crossings may be used in this way in the wavelength searching processes to determine an adapted Christiansen effect scattering wavelength selection for a given volume of analyzed space.

Figure 6:
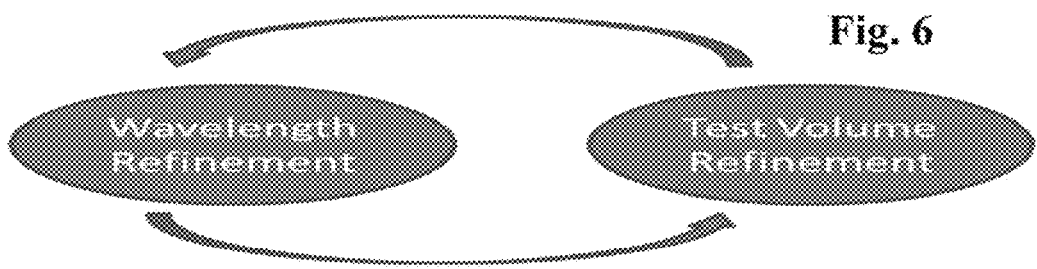
FIG. 6 shows an exemplary refinement process by which wavelength selection and refinement may take place iteratively with a refinement process for the test volume being analyzed.

FIG. 6 shows an exemplary refinement process by which wavelength selection and refinement may take place iteratively with a refinement process for the test volume being analyzed. For example, when the wavelength refinement process or a portion of the process or an iteration has been completed, an average metric parameter of the received light may be compared to a previously established threshold. Thereafter, the search volume may be refined for the next wavelength refinement scanning/searching process.

For example, if the average metric parameter for a scanned test volume is sufficiently large for the converged wavelength search band, then there may be too much near-range scattering contributions in the data to determine a good wavelength. In response, the test volume may be refined to refine and modify the near-range keep-out volume to remove more near-range scattering, such as extending the near-range keep-out minimum distance. In that example, refinement in test volume will thereafter sensitize future wavelength refinement processes to a test volume encompassing longer distances.

As another example, if the average metric parameter, M, is too small, the amount of sensed light within the analysis segments may be too small for accurate measurements. In this example, future test volumes may be adjusted to move the test volume closer to increase the returned and detected light at the image sensor. For example, the keep-out volume may be altered through moving either boundary, as described herein, in order to allow future wavelength analysis segments to include or to exclude nearer ranges for the test volume.

Figure 7:
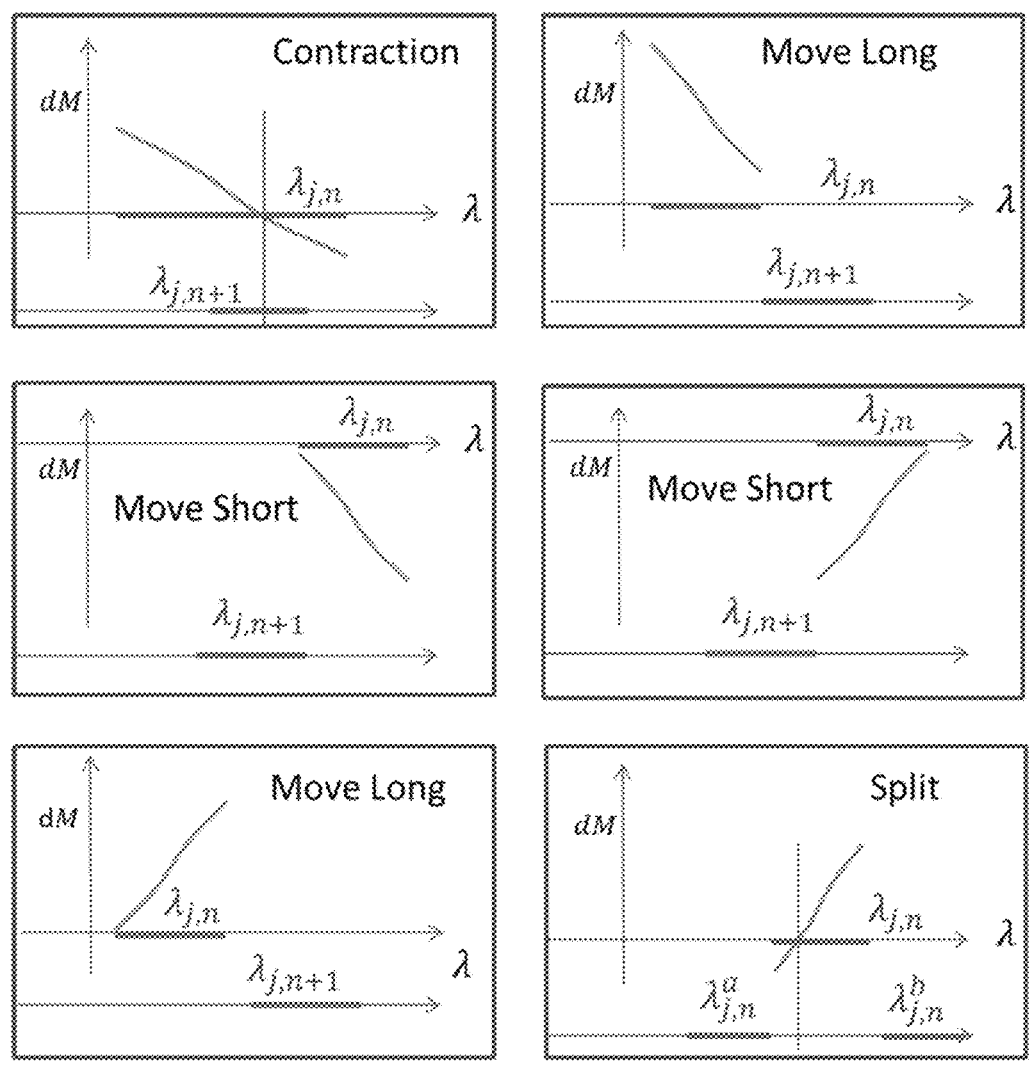
FIG. 7 illustrates examples of how the wavelength search bands may be updated based on gradient metric parameter curves.

FIG. 7 illustrates examples of how the wavelength search bands may be updated based on gradient metric parameter curves. Included are various examples of calculations of metrics and gradient metrics calculated for exemplary returned beams at different wavelengths. As described further herein, and as shown in the upper left-hand box, if the gradient metric curve has a negative slope and crosses zero for the wavelength band used, a new narrower search band may be selected that is centered at the zero-crossing.

In one embodiment, if the gradient metric $dM_{j,k}$ curve has all positive values, then the wavelength search band will be shifted to longer wavelengths. Alternatively, if the gradient metric curve has all negative values, then the wavelength search band is shifted to shorter wavelengths. Different scenarios are detailed herein, showing different gradient metrics and wavelength changes. The graphs show increases and decreases in wavelength as the ordinal for that wavelength search increments from $\lambda_{j,n}$ to $\lambda_{j,n+1}$. Responsive to these wavelength shifts, as described further herein, new search bands may be used for further wavelength searching.

In the embodiment shown, each graph in FIG. 7 has included therein a shorthand comment about the likely changes to the wavelength search band in creating the next wavelength search band. For example, the upper left corner graph shows a similar gradient metric to that described in further detail in FIG. 5, suggesting a "Contraction" of the next wavelength search band. The other notes in each graph suggest moving the wavelength search band to encompass longer wavelengths ("Move Long"), to encompass shorter wavelengths ("Move Short") and split the search bands into two future wavelength search bands. In another embodiment, the new search band(s) may have some wavelengths previously searched or in previous search bands. These determinations and strategies for shifting the wavelength search bands are further described herein.

Splitting into two future wavelength search bands involves a special case where the gradient metric curve has a positive slope and crosses zero. In one embodiment, this result for the gradient metric will result in two subsequent search bands being identified—a first new search band has longer wavelengths than the initial search band and a second new search band that has shorter wavelengths. Either the shorter wavelength search band or the longer wavelength search band may be used for the next wavelength search iteration. The other search band may be stored in a buffer for a later wavelength search iteration. Alternatively, if a sufficient number of tunable lasers are available, the process may be operated such that multiple disconnected wavelength search bands may be searched simultaneously.

Figure 8:
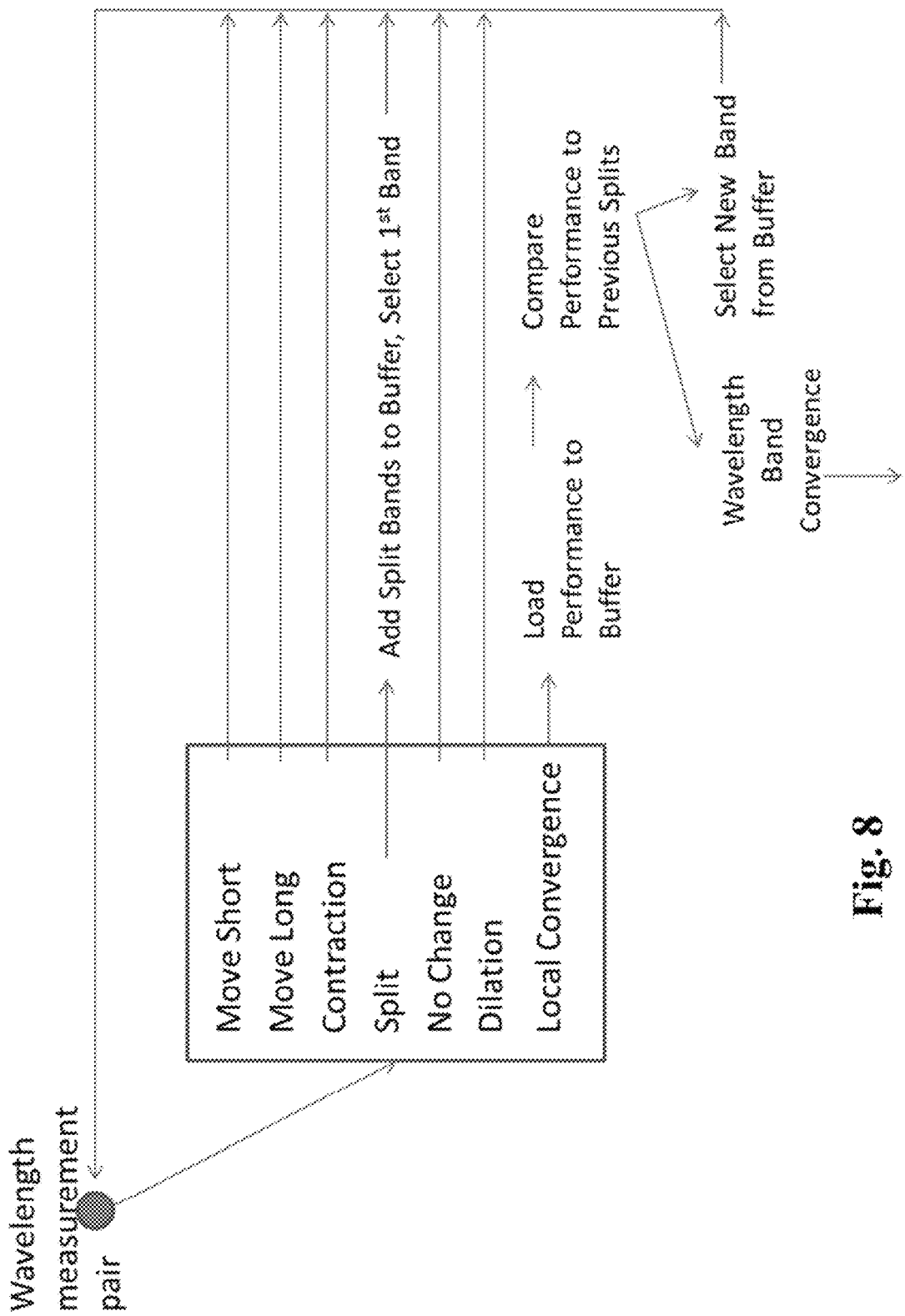
FIG. 8 shows more detail on an exemplary embodiment of a wavelength refinement process.

FIG. 8 shows more detail on an exemplary embodiment of a wavelength refinement process. As described further herein, after completing a wavelength measurement pair, the wavelength search band may be altered based on analysis of the metric and gradient metric data created thereby. The process to search different wavelength bands during an active Christiansen effect searching phase may be refined to include any of the search and refinement strategies described herein.

After a wavelength measurement pair of beams are received by the system, and their metrics and gradient metric have been calculated, a decision about the next wavelength band is determined as described further herein. Several options for this wavelength refinement have been described such as, moving to shorter wavelengths, moving to longer wavelengths, contracting the wavelength search band, and splitting the wavelength search band. Other options may include recognizing that local convergence has occurred (as previously discussed), that no change is required, or in some cases that a dilation or extension of the wavelength search band may be desired. Any of the cases may be selected if there is insufficient information to take the other actions. As described earlier, if a split in the search band is determined to be needed, one of the search band parameters may be placed on a buffer, such as the lower or upper search band suggested by the decision to split the search band.

Any unsearched wavelength search bands may retrieved from the buffer for the next measurement pair iteration. In one embodiment, the best performing wavelength search band is selected and finalized, if and when there are no remaining search bands on the buffer that have not yet been searched.

If local convergence has occurred, the performance parameters are saved to be later compared to previous locally converged performance measurements. As shown in FIG. 8, the comparison may cause a new band to be selected from the buffer or may cause convergence or finalization of the wavelength band for LIDAR use in the volume. In one embodiment, the best performing wavelength search band may be selected and finalized as the wavelength band before other search bands have been searched, such as if the performance value of the selected search band exceeds some threshold. In another embodiment, potential wavelength search bands are searched and performance values recorded for each split band or search before the wavelength band is finalized.

Figure 9:
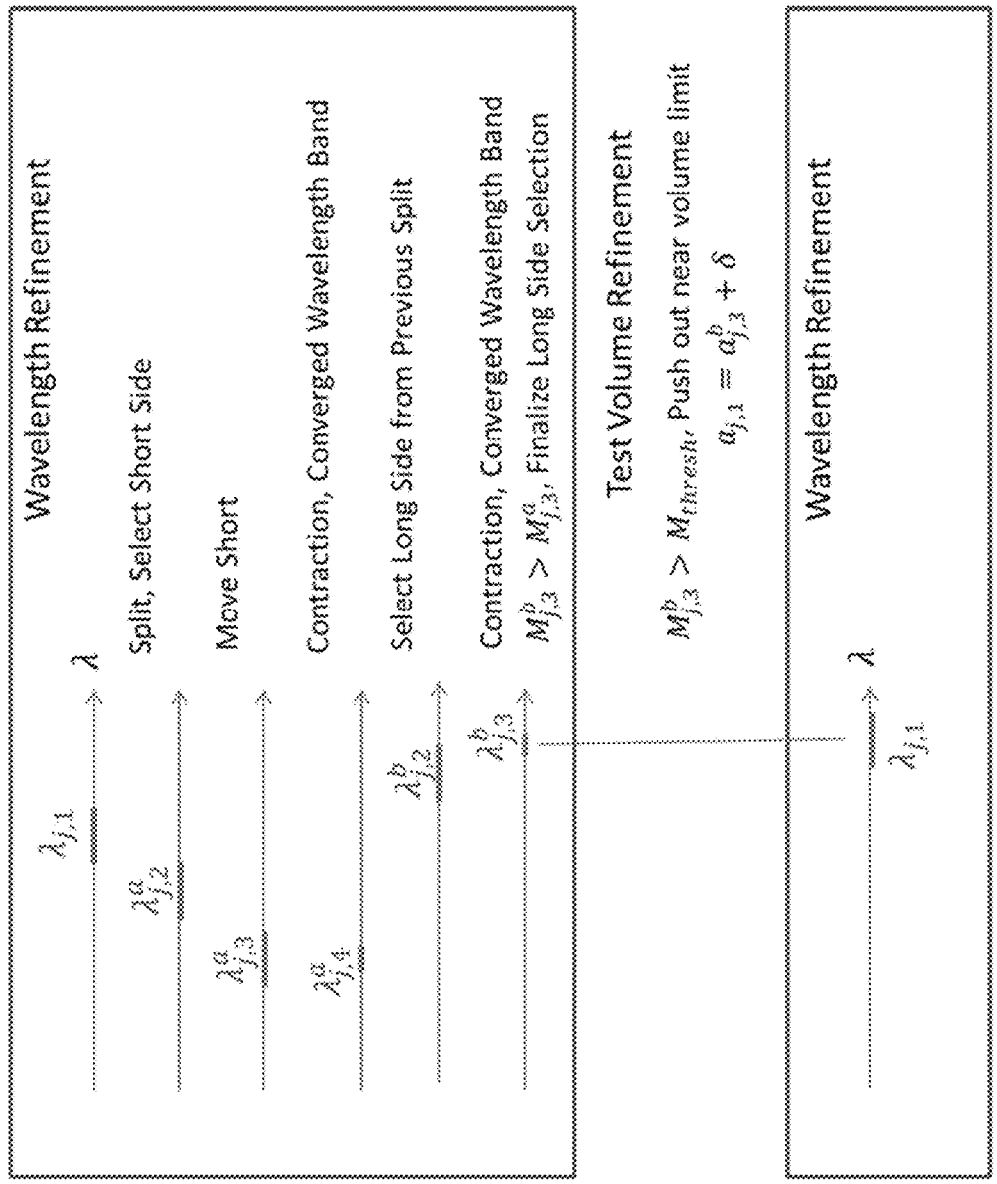
FIG. 9 illustrates exemplary embodiments of how wavelength search bands may evolve in time.

FIG. 9 illustrates exemplary embodiments of how wavelength search bands may evolve over time. In the illustrated example, a wavelength refinement process is described that includes selection of different adjustments to wavelength search bands across multiple iterations of wavelength pair measurements. However, other refinement processes may be extrapolated from this exemplary process.

For the example shown, based on a calculated gradient metric parameter curve, an initial search band spanned by $\lambda_{j,1}$ on the first line of FIG. 9 may have a positive slope and zero-crossing. As shown, this gradient metric parameter curve may cause a decision to split the subsequent wavelength search band as described further in FIG. 7. The shorter wavelength subsequent search band ($\lambda_{j,2}^a$) may be selected on the second line of FIG. 9, while parameters for the longer wavelength search band are stored in a buffer. After the next wavelength measurement pair, the calculated gradient metric parameter curve may be negative so that a shorter search band ($\lambda_{j,3}^a$) is selected on the third line of FIG. 9. With the next wavelength measurement pair, in this example, the gradient metric parameter curve has a negative slope and zero crossing so that a contracted search band ($\lambda_{j,4}^a$) centered about the zero crossing is selected on the fourth line of FIG. 9. When the contracted search band is as narrower as a predefined minimum search band width, local convergence is achieved and additional search bands that haven't been explored may be used. In this example, the search band ($\lambda_{j,2}^b$) from the initial split is loaded from the buffer and used for selecting wavelengths of the tunable laser on the fifth line of FIG. 9. If this search band has a negative slope and a zero crossing, subsequent search band iterations may converge about that zero crossing ($\lambda_{j,3}^b$).

In one embodiment, the local convergences during the wavelength selection process may be compared. For example, after the second local convergence has occurred, the average-metric parameters for the two locally-converged search bands may be compared. Based on the comparison, for example, the wavelength search band producing the highest metric value is selected as the best refined search band. In this example ($\lambda_{j,3}^b$) is selected as the finalized search band during the wavelength refinement process.

As an example of Test Volume Refinement, described further herein, $M_{j,3}^b$ is compared to $M_{Threshold}$ to determine whether the received metric value is greater than a threshold value, such as the maximum recordable received light. For example, this maximum may be relative to a given a gain value for the image sensor. As shown in the example in FIG. 9, when the measured metric is greater than the metric threshold value, the near volume limit may be extended, such as to exclude near-range scatterers.

After Test Volume Refinement, the Wavelength Refinement process element may be conducted again as illustrated near the bottom of FIG. 9. For this subsequent Wavelength Process, the initial wavelength search band ($\lambda_{j,1}$) may be initialized to the final wavelength band of the previous Wavelength Refinement iteration ($\lambda_{j,3}^b$).

Figure 10:
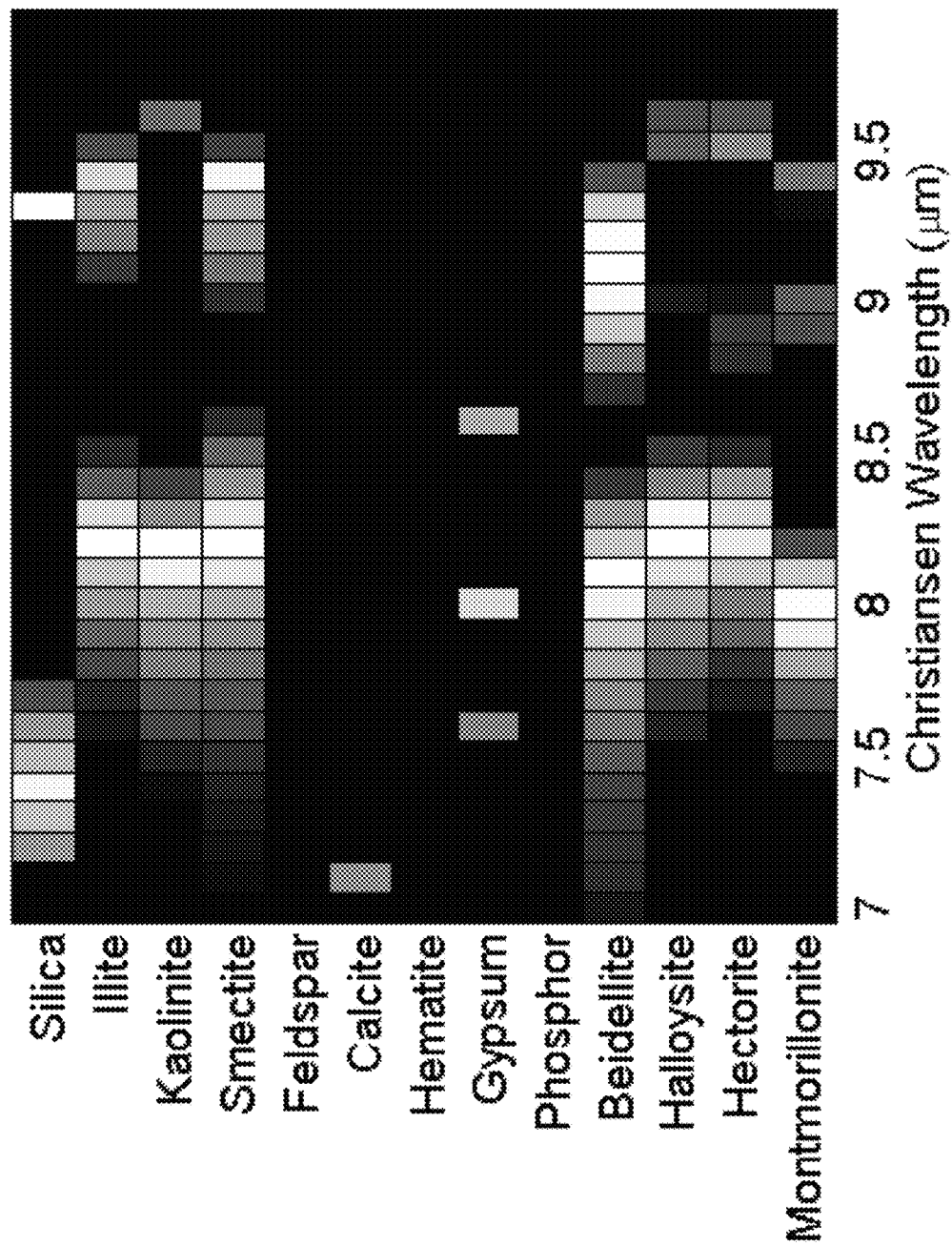
FIG. 10 shows wavelength bands near the Christiansen wavelength for several dust forming minerals.

FIG. 10 shows wavelength bands near the Christiansen wavelength for several dust-forming minerals. Wavelengths are indicated that result in an index of refraction between 0.95 and 1.05 when encountering dust of that material. The gray scale shown contrasting with the black image background show areas where the index of refraction resides within the range of 1.0 (e.g., between 0.95 and 1.05) for the specified wavelength. Tunable lasers for the described wavelength searching embodiments may be selected for reasons including covering the Christiansen wavelength of the likely scatterers to be encountered in the analyzed volume. For example, as shown, the wavelength range for the tunable lasers may likely include the wavelength 7.4 µm because silica dusts are likely to be encountered in some measure because quartz or silica is often the most abundant dust forming mineral. Most of the other minerals that appear in dusts have Christiansen wavelengths between 8 µm and 8.5 µm with relatively good overlap for low scattering. Dispersion curves for Feldspar, Hematite and Phosphous minerals were not found.

It doesn't appear from the Figure that the Christiansen effect will be very effective for dust distributions where Calcite is a major component. There is a Christiansen wavelength for Calcite near 7 µm that possibly could be used. However, because the atmospheric transmission is very poor at this wavelength, other processes or decisions can be used to compensate. For example, there are narrow transmission bands within the atmosphere that can provide acceptable short range performance.

Figure 11:
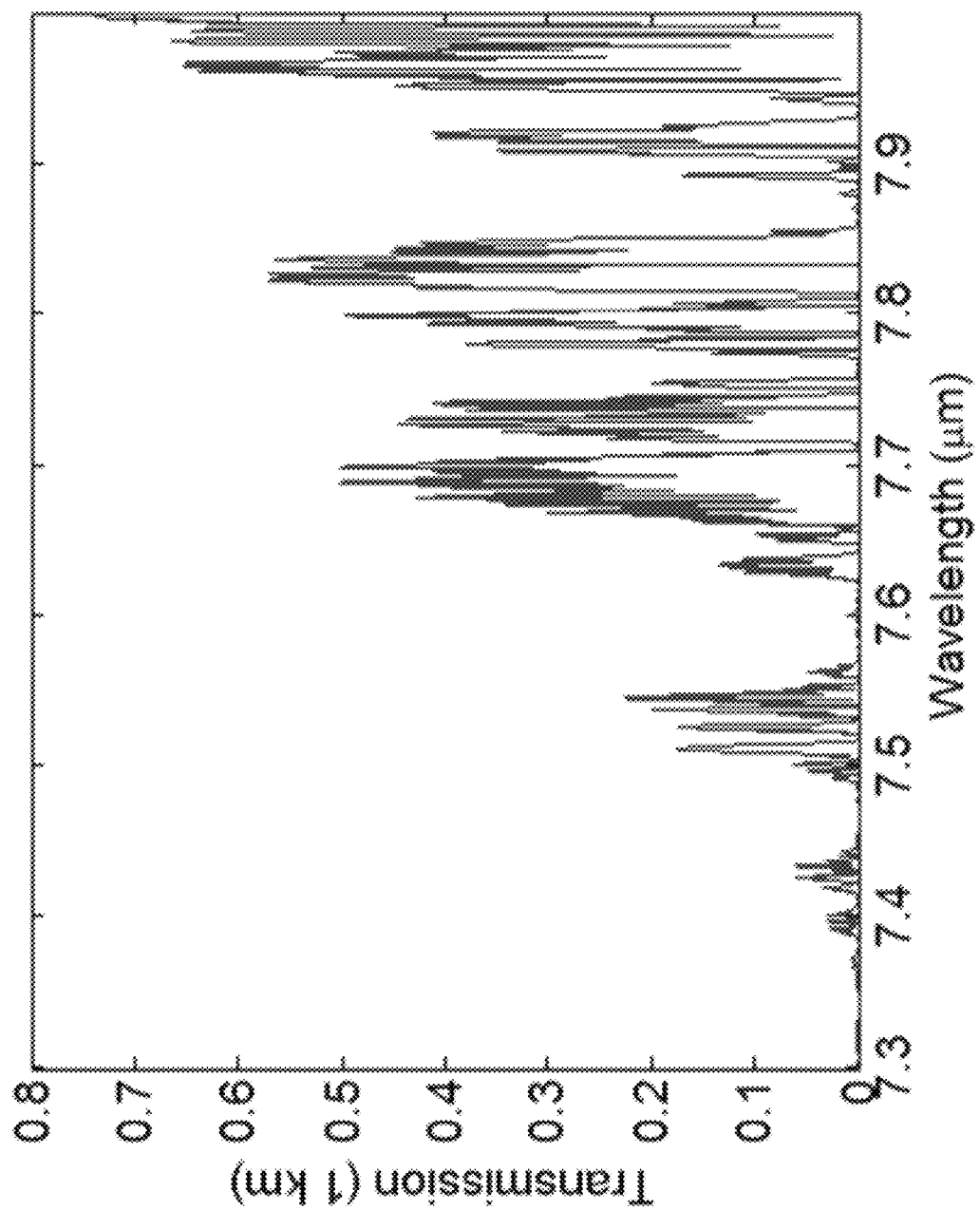
FIG. 11 shows the atmospheric transmission through the atmosphere over a 1 km range as a function of wavelength.

FIG. 11 shows the atmospheric transmission through the atmosphere over a 1 km range as a function of wavelength. The atmospheric transmission is calculated with Line-By-Line Radiative Transfer Model (LBLRTM) using a mid-latitude summer model. For typical remote sensing applications, a wavelength range including 7.4 µm and slightly longer wavelengths is not a favorable for LIDAR due to fall off of transmission through the atmosphere at ranges of 1 km. There is severely increasing attenuation at this range as wavelengths decreasing toward 7.4 µm, below the typical LWIR transmission band. However, as described further herein, the systems and methods will search for wavelengths to decrease scattering attenuation from dust, which dominates attenuation at long ranges and in dust-filled volumes.

Figure 12:
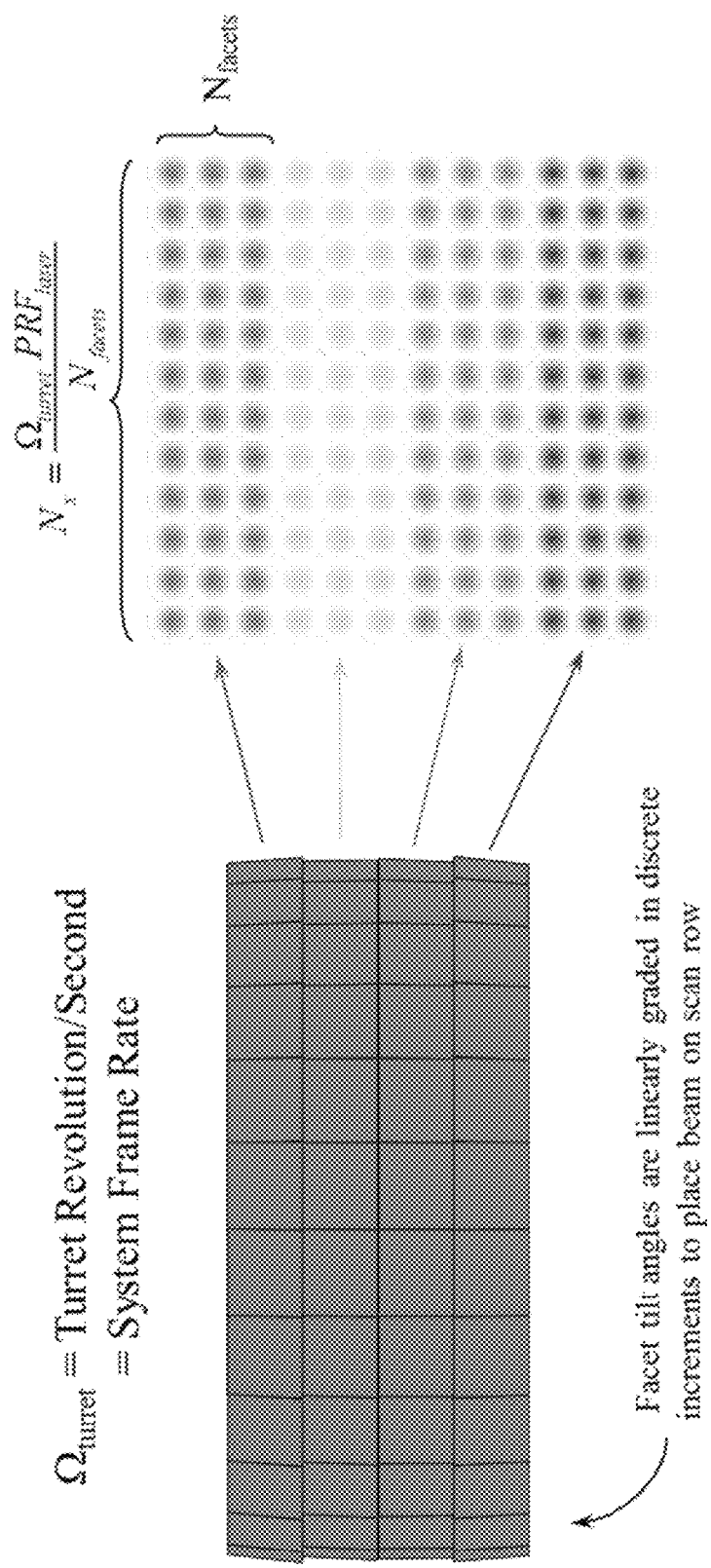
FIG. 12 illustrates an exemplary embodiment of a multi-polygon multi-beam scanner.

FIG. 12 illustrates an exemplary embodiment of a multi-polygon multi-beam scanner. In this embodiment, a multi layered polygon scanner may be designed so that each layer is used to scan a separate tunable laser. Each facet of the polygon sweeps the radiation beam direction across a sequence of horizontal angles, and a separate horizontal scanner may be used to angular displace each of the radiation beams in the vertical direction. The laser output may be modulated so that each beam path appears as a separate isolated line on the digital image.

Figure 13:
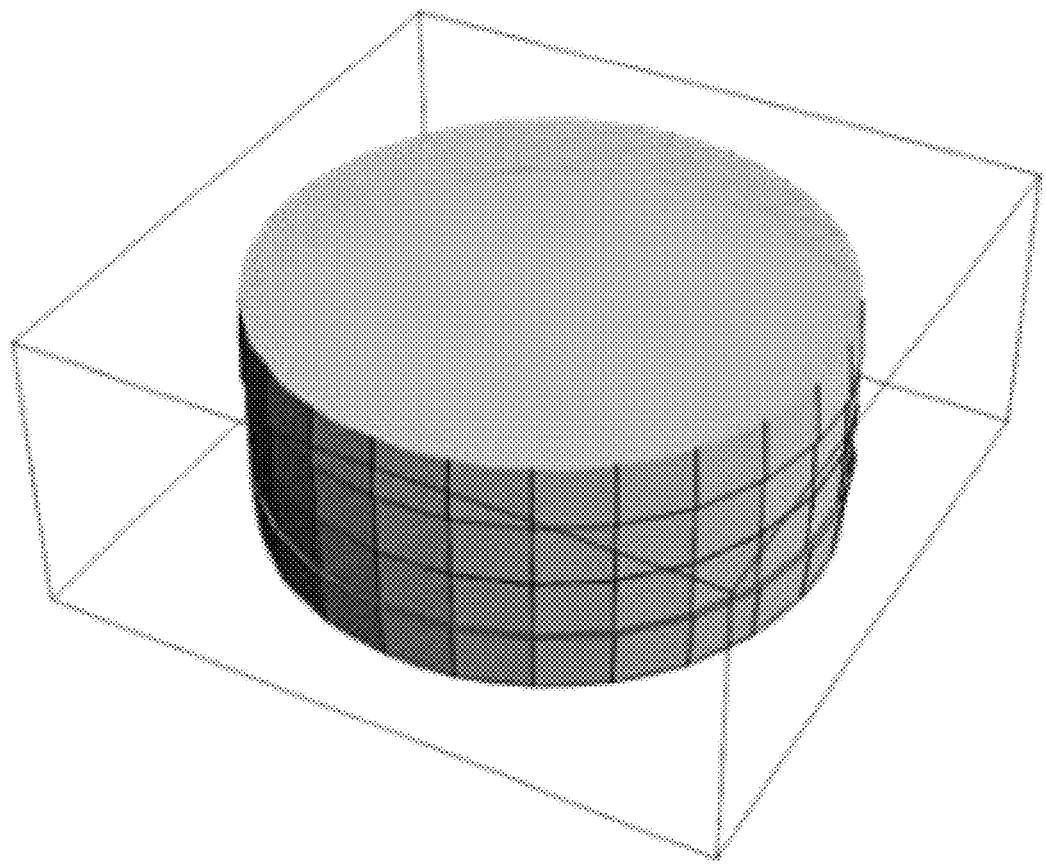
FIG. 13 illustrates further details of an exemplary embodiment of a multi-polygon multi-beam scanner.

FIG. 13 illustrates further details of an exemplary embodiment of a multi-polygon multi-beam scanner. The exemplary embodiment includes 100×100 pixels, 4-polygons with 25 facets each, and 25 rows scanned per polygon. The embodiment further includes 4μ-chip lasers operating at 10 kHz and a 4 Hz frame rate.

Figure 14:
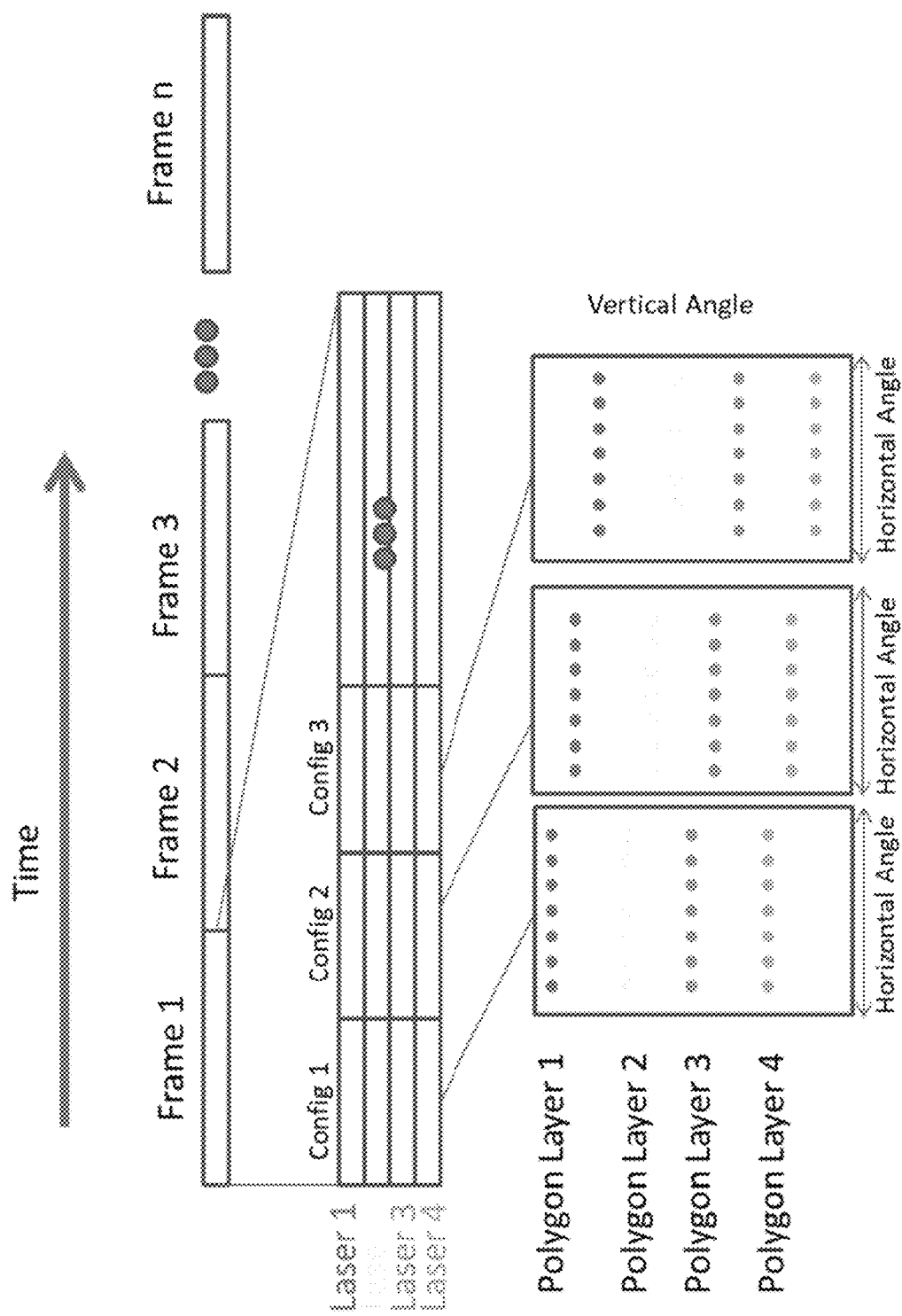
FIG. 14 additionally illustrates how an embodiment directs radiation beams through sequences of angles.

FIG. 14 additionally illustrates how an embodiment directs radiation beams through sequences of angles. In this embodiment, the camera collects one digital image per camera frame. Within each camera frame, the polygon scanner may complete one rotation or less than a complete rotation. In some embodiments, an entire scan frame may not be able to be captured in one image capture frame. For example, there may be too much overlap between beams to capture an entire scan frame in one capture frame.

In one embodiment, within one rotation, each laser experiences a horizontal sweep for every polygon facet from which it is reflected. However, after each horizontal sweep, the vertical angle of each of the radiation beams may be modified with a separate vertical angle configuration. This vertical angle modification may be performed with a separate scanner placed up-stream or down-stream from the multilayer polygon scanner, or through a tilt of the entire polygon scanner. In this embodiment, a full array of radiation beam lines is produced for each digital image frame.

Figure 15:
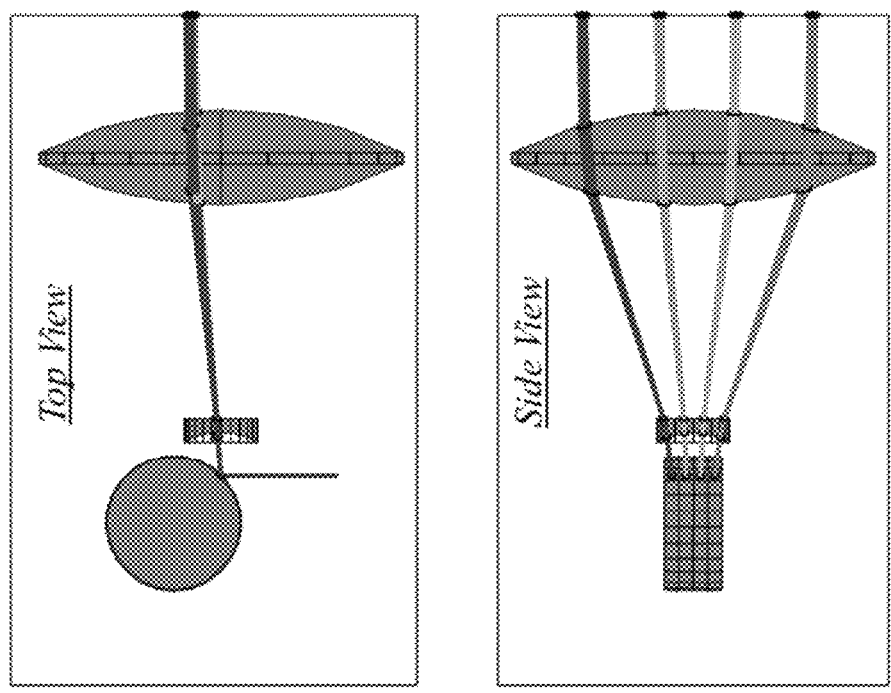
FIG. 15 illustrates embodiments of various additional design aspects of one multi-polygon, multi-beam scanner.
Figure 15:
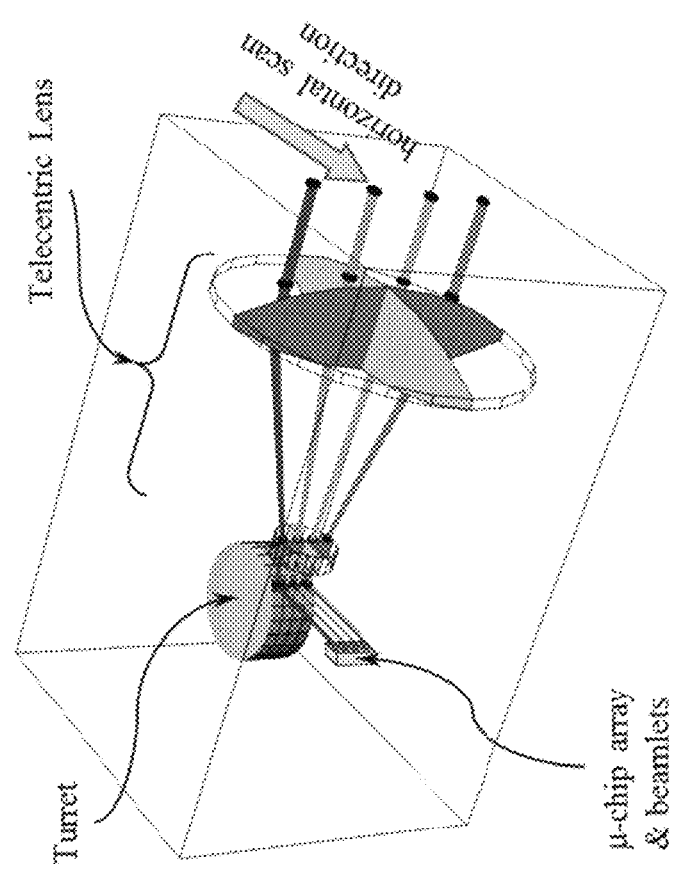

FIG. 15 illustrates embodiments of various additional design aspects of one multi-polygon, multi-beam scanner. In alternative embodiments, the detailed timing may be constructed in several different manners and multiple camera image frames may also be used for each polygon rotation. The specific camera frame rate, horizontal scan rate, and laser modulation rate, and their relative synchronization may be advantageously chosen to maximize the utilization of the two dimensional digital image while avoiding excessive overlap in the images of the separate radiation beam lines.

In the embodiment shown, a telecentric lens is used to simultaneously de-magnify the angular deflections of the radiation beams and magnify the beam size. The teleconcentric lens therefore reduces turret size by reducing scan angle, and magnifies beamlets to achieve the required spotsize. The combination of initial and final magnification of beamlets sets the beam size at the target. Other possible scanning methods may include additional spinning polygon(s) mechanisms, galvanometers, fast two-axis mirror, spinning Risley Prisms, or other scanning mechanisms that are well known in the art.

The imaging system described herein has a spectral range response that includes the wavelength range that is covered by the tunable lasers and wavelength controller. However, in several various embodiments, the background light recorded in the digital image is reduced by including spectral filter within the imaging system that explicitly blocks light outside of the utilized wavelength range. This increases the signal to noise ratio (SNR) for measurements of scattered light from each of the radiation beams.

In an embodiment further designed to reduce background radiation, a dynamically-controlled spectral filter is used within the imaging system. In this embodiment, the wavelength controller additionally controls the dynamically controlled spectral filter to provide high transmission at the selected wavelengths used by the one or more tunable lasers. However, at any given time, the dynamically controlled spectral filter may still highly attenuate wavelengths that are still within the overall systems wavelength range. The dynamically-controlled spectral filter may be implemented with dynamic Fabry-Perot filters well known in the art or through dynamically tilted interference filters. The coordinated control of a dynamically controlled spectral filter with the wavelength selection of the tunable lasers may be implemented with pre-tabulated calibration tables or with a separate sampling beam line and LWIR detector that can drive a feedback control loop.

Figure 16:
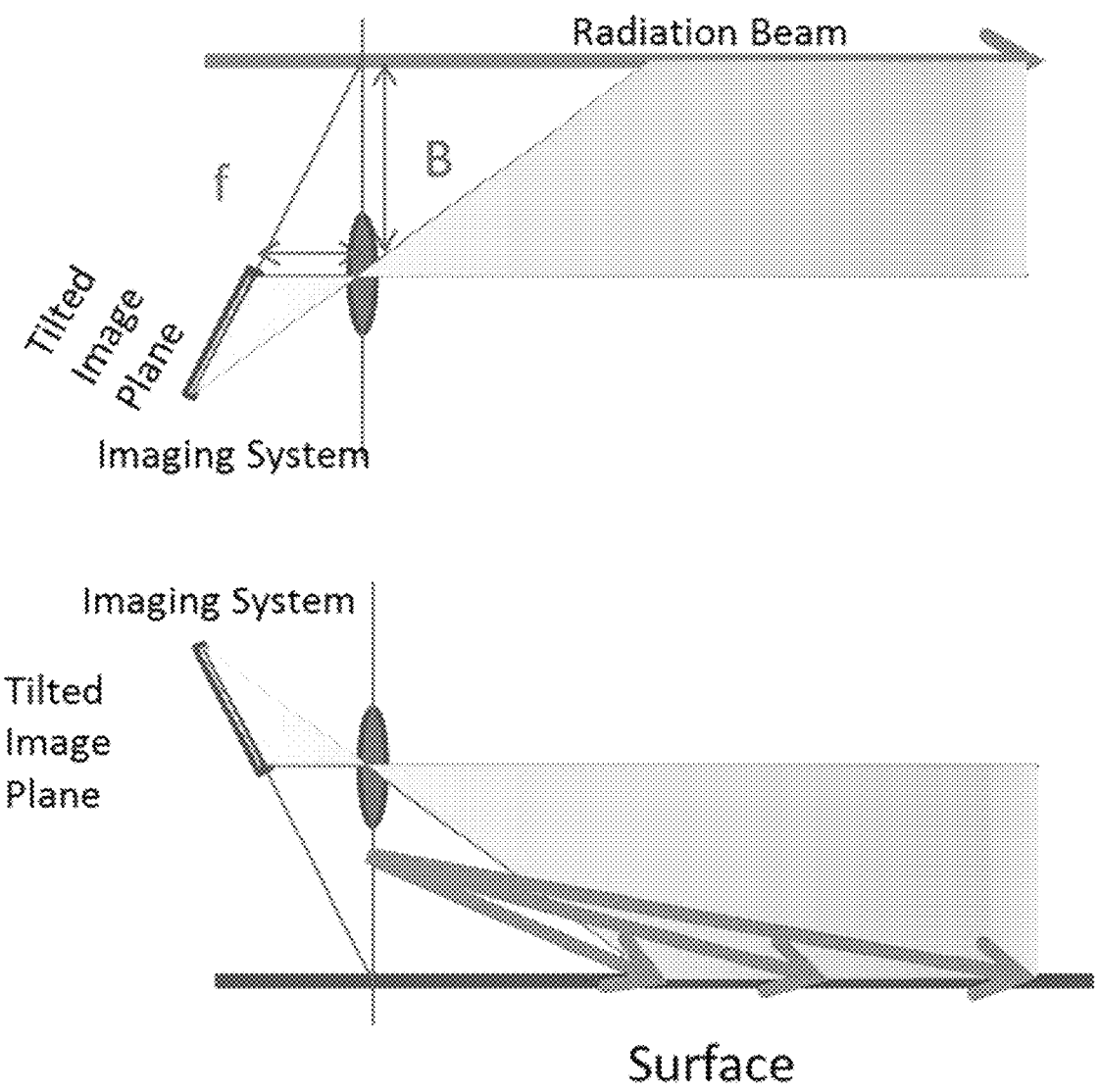
FIG. 16 illustrates how a tilted image plane may be used maintain a focused image for a radiation beam line or for surface scattering points along a relatively flat surface.

FIG. 16 illustrates how a tilted image plane may be used maintain a focused image for a radiation beam line or for surface scattering points along a relatively flat surface. The tilted image plane receives imaging input radiation through an entrance aperture that is offset from the image plane by a focal length (f) and offset from the exit aperture of by a bistatic distance (B).

In some sets of embodiments, the imaging system may be modified to provide sharper images for both near and far range images of scatter from radiation beams. Though the image illustrates a line in object space that is parallel to the optical axis of the imaging system, a tilted image plane may also be used to provide a focus corrected image for arbitrary lines in object space using an effect known as the Scheimpflug Principle.

In the embodiment depicted, in the upper frame of the image, a tilted image plane is used to maintain focus of particle and surface scatter resulting from a single radiation beam. In the lower frame, a tilted image plane is used to maintain focus of surface scatter resulting from multiple radiation beams.

In one embodiment, either configuration may be chosen as a fixed system that best accommodates the planned system scenarios. In other embodiments, a system may be able to adjust dynamically the effective location of the tilted image plane to accommodate either sequential selections of radiation beams or a dynamically-varying relative surface location. In these embodiments, a system may be able to adapt configurations to best suit the conditions of the measured volume, such as through using multiple radiation beams, as described further herein.

Figure 17:
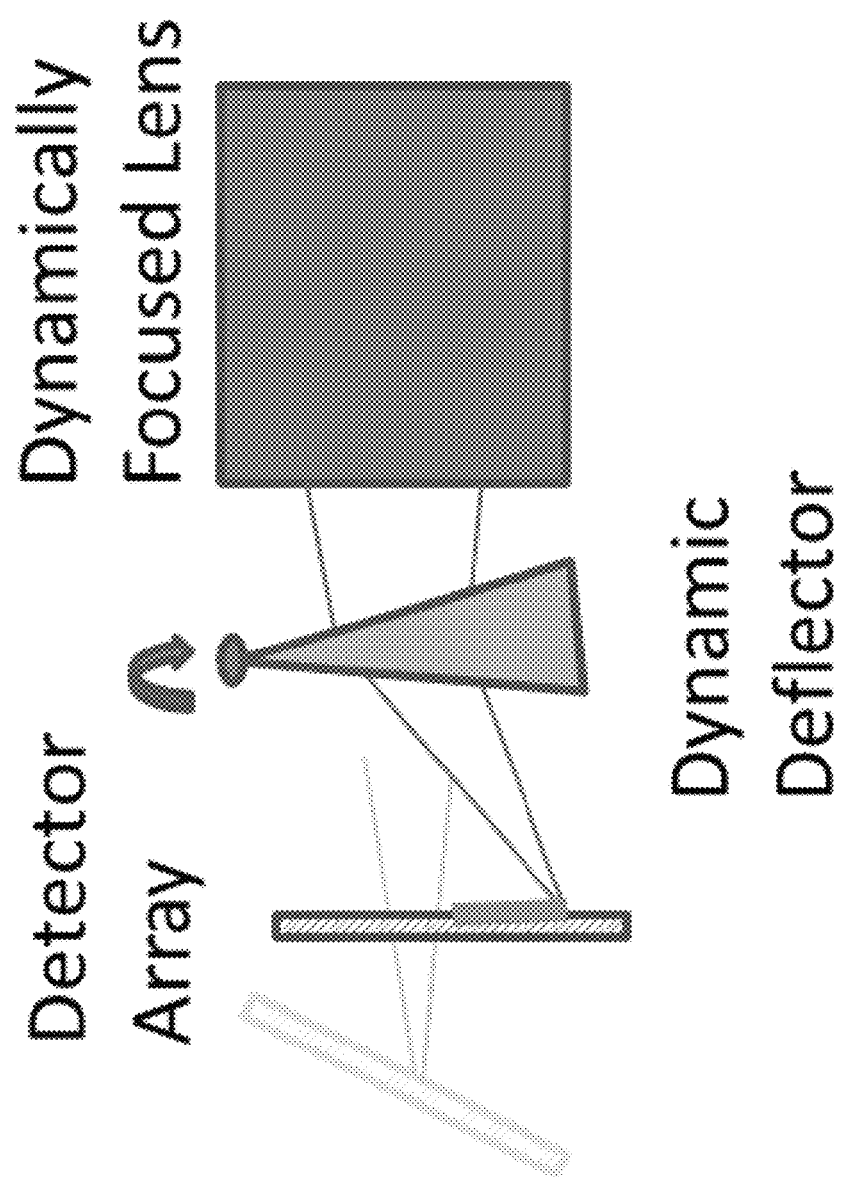
FIG. 17 shows a system including a conventional dynamic focus system coupled with a dynamic image deflector, in this embodiment, implemented with a prism.

FIG. 17 shows a system including a conventional dynamic focus system coupled with a dynamic image deflector, in this embodiment, implemented with a prism. One simple implementation is shown to optically implement a dynamically controlled effective tilted image array (e.g., detector array). By controlling the focus and image deflection of the system, a virtual tilted image plane may be adjusted without moving the focusing lens mount or detector array relative to the overall imaging system mount.

The depicted dynamic lens system is dynamically controlled to adjust the image plane tilt and position and optimize the digital image sharpness of surface scatter points and/or particle scatter. This optimization may be based on pre-tabulated system calibration parameters, known scan angles, and/or measured surface ranges.

Figure 18:
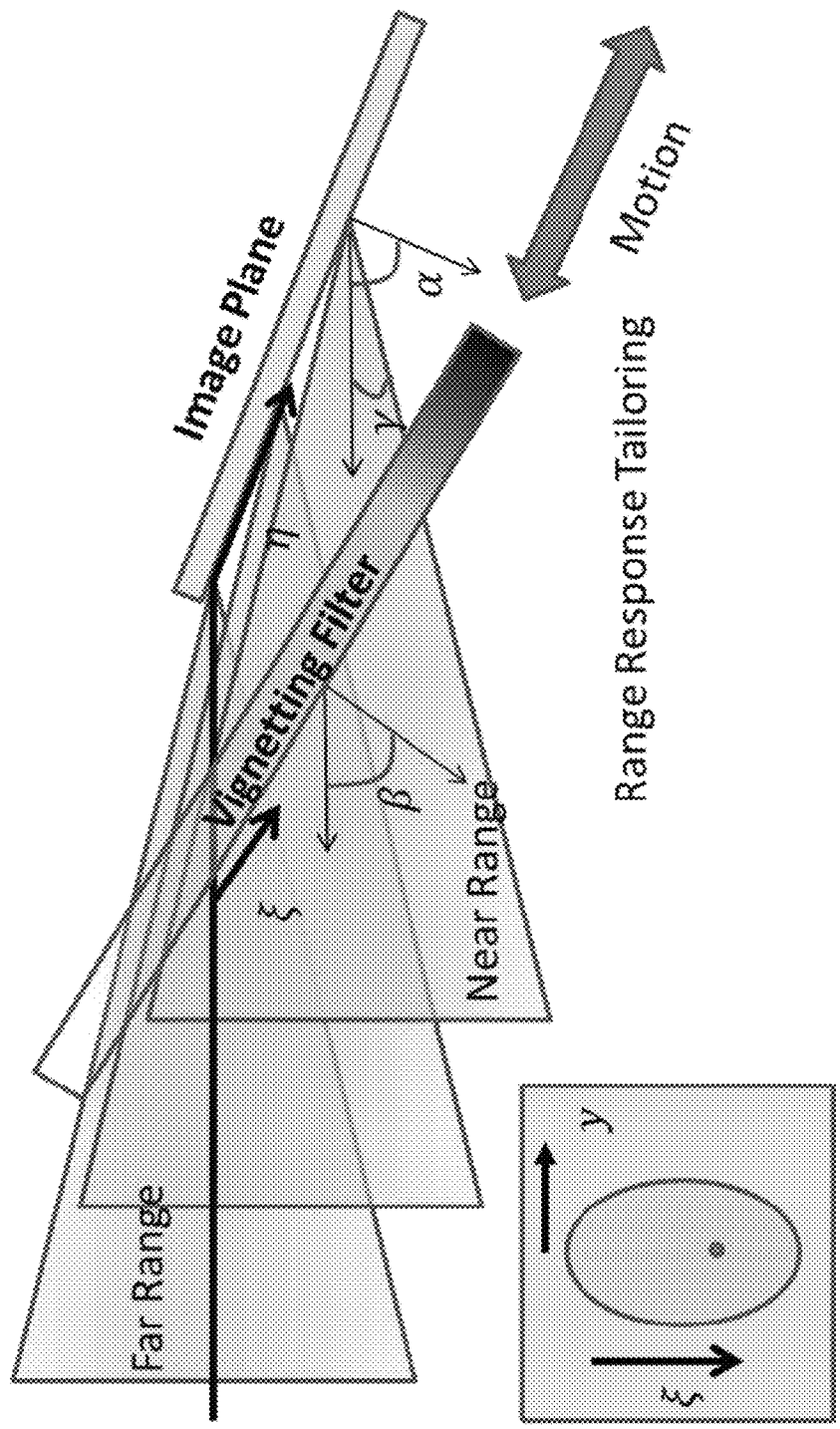
FIG. 18 shows one embodiment combined with a tilted image plane.

FIG. 18 shows one embodiment combined with a tilted image plane. In this embodiment, a vignetting filter is positioned on a plane at an angle from the image plane. This approach may also be used for embodiments other than tilted image plane embodiments.

Cones of light coming to focus as at different position on the image plane correspond to different ranges and cross the vignetting filter plane at different locations. By providing a position dependent attenuation (e.g., a gradient or variable density filter) on or near the vignetting filter plane, the near range scattering sources may be attenuated by a much greater proportion than the far range scattering sources. This vignetting filter may further be implemented simply as a blade or hard aperture or asymmetric vignetting aperture.

In some embodiments, near range backscatter from radiation beam lines may produce much brighter intensities at the image plane than the intensities produced from long range scatter. To avoid image saturation in the digital images from near range images while maximizing the overall gain of the system to benefit long range detection, it may be desirable to include optical range response tailoring through static or dynamic asymmetric vignetting.

To accommodate variations in scattering conditions, the vignetting filter may be dynamically controlled. One simple implementation for dynamic motion is shown in FIG. 17, where the filter simply moves along the vignetting plane. This motion allows for a dynamic range manager to suppress bright near range sources to various extents while increasing the imagers gain to detect far range scattering events.

Figure 19:
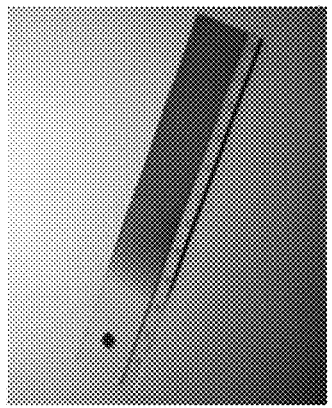
FIG. 19 shows a variable density filter for use in an embodiment.

FIG. 19 shows a variable density filter. A variable density filter may be used to reduce near-range backscatter using a gradient density filter. In one embodiment, a variable density filter may be used in a tilted image plane embodiment as described in FIG. 18.

Figure 20:
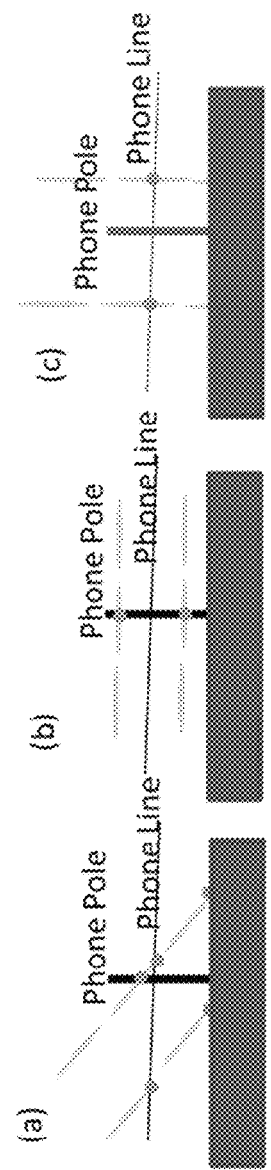
FIG. 20 illustrates an example of different scan orientations and resulting detections.

FIG. 20 illustrates an example of different scan orientations and resulting detections.

Many natural and man-made objects and features may be dominantly horizontal or vertical. For example, man-made items like phone poles and phone lines may have both horizontal and vertical structures. With laser modulation, the radiation beam lines exposed on to the digital images will generally have asymmetry due to the angular extent of scanning that occurs for each laser pulse. If no laser modulation is used, a certain degree of angular seep may be expected to occur on the radiation beams during the camera integration time.

This asymmetry in the shape of the radiation beams may be utilized to enhance detection of narrow vertical or horizontal structures by simply orienting the beam scanning mechanism so that the sequences of angles in the fastest angular sweeping direction are along paths that are neither substantially parallel nor perpendicular to the horizon. In the example shown in FIG. 20, frame (b) shows that sweeps parallel to the horizon are likely to miss phone lines, whereas frame (c) shows that vertical sweeps are likely miss phone poles. In frame (a), diagonal sweeps are used to increase the odd of detecting both phone poles and phone lines.

In one embodiment, the polarizations of the one or more tunable lasers are oriented to have an angle that is neither parallel nor perpendicular to a primary scattering plane. The primary scattering plane is defined herein by the vector from the exit aperture to the entrance aperture and the mean direction of each output radiation beam. The bistatic orientation of the imaging system is sensitized to receive scatter in the primary scattering plane. It is expected that light that is polarized parallel or perpendicular to the primary scattering plane before scattering will mostly remain polarized parallel or perpendicular (respectively) to the primary scattering plane after scattering.

By choosing the laser polarization to have an exit polarization state that is diagonal to the scattering plane, and by matching a polarizing filter within the imaging system, there will be reduced intensity from near range scatterers and this design may be used to assist in dynamic range management. Alternatively, scattered images may be enhanced by selecting matched polarizations for the tunable lasers and imaging system where both polarization states (e.g., exit polarization state and scattered polarization state) and perpendicular to the primary scattering plane. Of course, polarizations of background sources Fresnel reflections from scattering surfaces may also impact the selection of laser polarization imaging system polarization filters.

It will be understood that there are several extensions from the presented systems and methods that may be derived via combination with other LIDAR and optical techniques. Though this disclosure describes a static imaging approach for extracting range, a coherent (heterodyne) detection scheme is also readily feasible with presently described and available laser and detector technology. This approach is attractive in that it does not require either high peak power short pulse lasers or high bandwidth detectors.

Much of the challenge associated with speckle for coherent detection is less restrictive for LWIR due to the longer wavelengths. Example architectures may include FMCW where a chirped laser optical frequency is coherently mixed with a local oscillator to produce an electrical signal. Spectral analysis of the electrical signal is used to extract scattering signals as a function of range which may be utilized to optimize the wavelength controller and all other system control aspects as presently described.

The present disclosure has provided descriptions with a single imaging system entrance aperture and a single exit aperture associated with the beam scanning mechanism. However the disclosure is not limited to that case, and may include systems with multiple apertures. By utilizing multiple exit apertures or multiple entrance apertures, greater flexibility in optimizing the use of the digital images for better range triangulation and reduced spatial overlap interference may be afforded.

This patent description and drawings are illustrative and are not to be construed as limiting. It is clear that many modifications and variations of this embodiment can be made by one skilled in the art without departing from the spirit of the novel art of this disclosure. While specific parameters, device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. An optical system, comprising:
   one or more tunable lasers operable to provide radiation beams having selectable wavelengths within a wavelength range;
   a beam scanning mechanism operable to direct one or more radiation beams through sequences of angles, where the beam scanning mechanism includes an exit aperture for emission of the radiation beams;
   an imaging system, sensitive to the wavelength range, that is adapted to generate digitized images of scattering from particles or surfaces impinged by the radiation beams, wherein the imaging system further includes an entrance aperture different from the exit aperture;
   a wavelength controller that is configured to select wavelengths of the one or more tunable lasers to optimize the digitized images of scattering from particles or surfaces impinged by the radiation beams; and
   an image processor that is configured to use the digitized images to generate calculated volumetric coordinates of points where the radiation beams impinge surfaces;
   wherein the beam scanning mechanism is a multi-polygon, multi-beam scanner.

2. The optical system of claim 1, wherein the multi-polygon, multi-beam scanner includes a telecentric lens system configured to de-magnify angular deflections of radiation beams and magnify beam sizes of the radiation beams.

3. An optical system, comprising:
one or more tunable lasers operable to provide radiation beams having selectable wavelengths within a wavelength range;
a beam scanning mechanism operable to direct one or more radiation beams through sequences of angles, where the beam scanning mechanism includes an exit aperture for emission of the radiation beams;
an imaging system, sensitive to the wavelength range, that is adapted to generate digitized images of scattering from particles or surfaces impinged by the radiation beams, wherein the imaging system further includes an entrance aperture different from the exit aperture;
a wavelength controller that is configured to select wavelengths of the one or more tunable lasers to optimize the digitized images of scattering from particles or surfaces impinged by the radiation beams; and
an image processor that is configured to use the digitized images to generate calculated volumetric coordinates of points where the radiation beams impinge surfaces;
wherein the image processor is further configured to use information about a relative orientation and a relative position of the entrance aperture and the exit aperture along with the sequences of angles to calculate volumetric coordinates associated with digital images of scattering from particles or surfaces impinged by the radiation beams.

4. An optical system, comprising:
one or more tunable lasers operable to provide radiation beams having selectable wavelengths within a wavelength range;
a beam scanning mechanism operable to direct one or more radiation beams through sequences of angles, where the beam scanning mechanism includes an exit aperture for emission of the radiation beams;
an imaging system, sensitive to the wavelength range, that is adapted to generate digitized images of scattering from particles or surfaces impinged by the radiation beams, wherein the imaging system further includes an entrance aperture different from the exit aperture;
a wavelength controller that is configured to select wavelengths of the one or more tunable lasers to optimize the digitized images of scattering from particles or surfaces impinged by the radiation beams; and
an image processor that is configured to use the digitized images to generate calculated volumetric coordinates of points where the radiation beams impinge surfaces;
wherein the wavelength controller is further configured to select iteratively wavelengths of the one or more tunable lasers to maximize intensity of images of scattering from particles or surfaces impinged by the radiation beams, wherein the particles or surfaces are selected to have calculated volumetric coordinates outside of a pre-selected volume.

5. The optical system of claim 4, wherein the pre-selected volume includes all points within a selected range of distances from either the exit aperture or the entrance aperture.

6. An optical system, comprising:
one or more tunable lasers operable to provide radiation beams having selectable wavelengths within a wavelength range;
a beam scanning mechanism operable to direct one or more radiation beams through sequences of angles, where the beam scanning mechanism includes an exit aperture for emission of the radiation beams;
an imaging system, sensitive to the wavelength range, that is adapted to generate digitized images of scattering from particles or surfaces impinged by the radiation beams, wherein the imaging system further includes an entrance aperture different from the exit aperture;
a wavelength controller that is configured to select wavelengths of the one or more tunable lasers to optimize the digitized images of scattering from particles or surfaces impinged by the radiation beams; and
an image processor that is configured to use the digitized images to generate calculated volumetric coordinates of points where the radiation beams impinge surfaces;
wherein the wavelength controller is further adapted to select iteratively wavelengths of said one or more tunable lasers to maximize a calculated intensity at a range threshold based on estimates of volumetric laser scatter and absorption.

7. An optical system, comprising:
one or more tunable lasers operable to provide radiation beams having selectable wavelengths within a wavelength range;
a beam scanning mechanism operable to direct one or more radiation beams through sequences of angles, where the beam scanning mechanism includes an exit aperture for emission of the radiation beams;
an imaging system, sensitive to the wavelength range, that is adapted to generate digitized images of scattering from particles or surfaces impinged by the radiation beams, wherein the imaging system further includes an entrance aperture different from the exit aperture;
a wavelength controller that is configured to select wavelengths of the one or more tunable lasers to optimize the digitized images of scattering from particles or surfaces impinged by the radiation beams; and
an image processor that is configured to use the digitized images to generate calculated volumetric coordinates of points where the radiation beams impinge surfaces;
wherein the one or more tunable lasers are configured so as to provide radiation beams with exit polarization states, such that scattered polarization states resulting from scatter from particles at pre-specified distances entering the imaging system are altered from the exit polarization states;
and wherein the imaging system further includes a polarization filter which suppresses transmission of light with polarizations different from the exit polarization states.

8. An optical system, comprising:
one or more tunable lasers operable to provide radiation beams having selectable wavelengths within a wavelength range;
a beam scanning mechanism operable to direct one or more radiation beams through sequences of angles, where the beam scanning mechanism includes an exit aperture for emission of the radiation beams;
an imaging system, sensitive to the wavelength range, that is adapted to generate digitized images of scattering from particles or surfaces impinged by the radiation beams, wherein the imaging system further includes an entrance aperture different from the exit aperture;
a wavelength controller that is configured to select wavelengths of the one or more tunable lasers to optimize the digitized images of scattering from particles or surfaces impinged by the radiation beams; and an image processor that is configured to use the digitized images to generate calculated volumetric coordinates of points where the radiation beams impinge surfaces;

wherein the imaging system further includes an asymmetric vignetting aperture configured to attenuate portions of the digitized images.

9. The optical system of claim 8, wherein the asymmetric vignetting aperture is adapted to be dynamically controlled, and wherein the optical system further includes:

a dynamic range manager operable to control the asymmetric vignetting aperture and a gain of the imaging system.

\* \* \* \* \*